US012440679B2

(12) United States Patent
Bink et al.

(10) Patent No.: US 12,440,679 B2
(45) Date of Patent: Oct. 14, 2025

(54) ELECTRIC STIMULATION SYSTEM

(71) Applicant: Medtronic, Inc., Minneapolis, MN (US)

(72) Inventors: Hank Bink, Golden Valley, MN (US); Erik J. Peterson, Fridley, MN (US); Louis Vera-Portocarrero, St. Anthony, MN (US); Vinod Sharma, Maple Grove, MN (US); Jiashu Li, Mounds View, MN (US)

(73) Assignee: Medtronic, Inc., Minneapolis, MN (US)

( * ) Notice: Subject to any disclaimer, the term of this patent is extended or adjusted under 35 U.S.C. 154(b) by 658 days.

(21) Appl. No.: 17/651,705

(22) Filed: Feb. 18, 2022

(65) Prior Publication Data

US 2022/0266028 A1 Aug. 25, 2022

Related U.S. Application Data

(60) Provisional application No. 63/152,867, filed on Feb. 24, 2021.

(51) Int. Cl.
*A61N 1/36* (2006.01)

(52) U.S. Cl.
CPC ..... *A61N 1/36139* (2013.01); *A61N 1/36171* (2013.01)

(58) Field of Classification Search
CPC ............ A61N 1/36139; A61N 1/36171; A61N 1/36062; A61N 1/36135; A61N 1/36146
See application file for complete search history.

(56) References Cited

U.S. PATENT DOCUMENTS

| | | | |
|---|---|---|---|
| 8,032,229 B2 | 10/2011 | Gerber et al. | |
| 10,183,168 B2 | 1/2019 | Baru et al. | |
| 2014/0350636 A1 | 11/2014 | King et al. | |
| 2019/0022397 A1 | 1/2019 | Srivastava et al. | |
| 2019/0209844 A1 | 7/2019 | Esteller et al. | |
| 2019/0388692 A1 | 12/2019 | Dinsmoor et al. | |
| 2020/0038660 A1 | 2/2020 | Torgerson | |
| 2020/0171313 A1 | 6/2020 | Dinsmoor et al. | |
| 2020/0179688 A1 | 6/2020 | Su | |
| 2020/0261722 A1* | 8/2020 | Alataris | A61N 5/0603 |
| 2020/0384270 A1* | 12/2020 | Doan | A61N 1/36167 |
| 2021/0008371 A1* | 1/2021 | Annecchino | A61N 1/36071 |

* cited by examiner

*Primary Examiner* — Eugene T Wu
(74) *Attorney, Agent, or Firm* — Shumaker & Sieffert, P.A.

(57) ABSTRACT

An example method of cycling electric stimulation includes delivering, via an implantable device, electric stimulation to a patient in accordance with a first therapy program; monitoring, via the implantable device and while the electric stimulation is being delivered in accordance with the first therapy program, a biomarker; and responsive to determining the biomarker satisfies a threshold, delivering, via the implantable device, electric stimulation to the patient in accordance with a second therapy program that is different than the first therapy program.

21 Claims, 13 Drawing Sheets

ELECTRIC STIMULATION SYSTEM

This application claims the benefit of U.S. Provisional Application Ser. No. 63/152,867, filed Feb. 24, 2021, the entire content of which is incorporated herein by reference.

TECHNICAL FIELD

This disclosure generally relates to medical devices, and more specifically, electrical stimulation.

BACKGROUND

Electrical stimulation devices, sometimes referred to as neurostimulators or neurostimulation devices, may be external to or implanted within a patient, and configured to deliver electrical stimulation therapy to various tissue sites to treat a variety of symptoms or conditions such as chronic pain, tremor, Parkinson's disease, epilepsy, or other neurological disorders, urinary or fecal incontinence, sexual dysfunction, obesity, or gastroparesis. An electrical stimulation device may deliver electrical stimulation therapy via electrodes, e.g., carried by one or more leads, positioned proximate to target locations associated with the brain, the spinal cord, pelvic nerves, tibial nerves, peripheral nerves, the gastrointestinal tract, or elsewhere within a patient. Stimulation proximate the spinal cord, proximate the sacral nerve, within the brain, and proximate peripheral nerves is often referred to as spinal cord stimulation (SCS), sacral neuromodulation (SNM), deep brain stimulation (DBS), and peripheral nerve stimulation (PNS), respectively.

A physician or clinician may select values for a number of programmable stimulation parameters in order to define the electrical stimulation therapy to be delivered by the implantable stimulator to a patient. For example, the physician or clinician may select one or more electrodes, polarities of selected electrodes, a voltage or current amplitude, a pulse width, and a pulse frequency as stimulation parameters. A set of therapy stimulation parameters, such as a set including electrode combination, electrode polarity, amplitude, pulse width and pulse frequency, may be referred to as a therapy program in the sense that they define the electrical stimulation therapy to be delivered to the patient.

SUMMARY

In general, the disclosure describes techniques for controlling electric stimulation, e.g., neurostimulation, that is delivered based on one or more measured biomarkers. Typically, an electric stimulation program, e.g., the amount of on-time and off-time of delivery of electric stimulation, the electrodes used to deliver the electric stimulation, and the parameters of the electric stimulation such as amplitude, frequency, pulse width, etc., is determined by trial and error. For example, the amount of on-time relative to off-time for a given period of time of electric stimulation, which electrodes are used for electric stimulation delivery, and the parameters of the electric stimulation, may be changed based on determining that the patient needs more or less electric stimulation. A user and/or clinician may then reprogram the electric stimulation with new parameters and new cycling on/off times. As such, the delivery of electric stimulation is fairly static and is not easily changed and/or reprogrammed based on the current state and/or needs of the patient. Consequently, the patient may be over- or under-stimulated and a device delivering the electric stimulation may not be being efficiently used and may consume more power than necessary to achieve a particular patient state, thereby reducing battery life.

In accordance with one or more techniques of this disclosure, a system may toggle between a plurality of electric stimulation programs, based the response of one or more monitored and/or measured biomarkers, to deliver electric stimulation to a patient via an implanted device. For example, an implanted device may deliver electric stimulation in accordance with a first therapy program, monitor a biomarker, and responsive to determining the biomarker satisfies a threshold, deliver electric stimulation to the patient in accordance with a second therapy program. In some examples, the one or more biomarkers may include a direct measure of patient symptoms, such as a patient's pain and/or pain score.

In some example, the one or more biomarker may include other measures, such as an accelerometer measurement indicating a patient's movement and/or position, a pressure sensor, a physiological signal, a cardiac signal, a respiratory signal, a body temperature, a patient posture, a blood flow measurement, an evoked compound action potential (ECAP), and any other suitable biomarker suitable for determining the efficacy of electric stimulation and/or other aspects of therapy, e.g., stimulation feeling, unintended side-effects, and the like. In some examples, the first electric stimulation therapy program may be an "on" program comprising predetermined on-off times, electrodes, and parameters, and the second electric stimulation therapy program may be an "off" program, conserving power consumption and battery life of the implantable device and preventing over-stimulation of the patient. In other words, the system may determine that patient needs electric stimulation based on one or more biomarkers and deliver the stimulation accordingly, the system may subsequently determine that the patient no longer needs the electric stimulation based on one or more biomarkers and turn stimulation "off" and/or deliver electric stimulation in accordance with a "no stimulation" therapy program, and may then subsequently determine that the patient needs electric stimulation again based on one or more biomarkers and deliver electric stimulation again. In some examples, the system may determine which of a plurality of electric stimulation programs to deliver to the patient based on one or more biomarkers, e.g., different stimulation levels such as "high," "medium," "low," "off," and/or any other level and/or number of varying electric stimulation programs, and delivery the determined electric stimulation program accordingly.

In one example, this disclosure describes a method of cycling electric stimulation includes delivering, via an implantable device, electric stimulation to a patient in accordance with a first therapy program; monitoring, via the implantable device and while the electric stimulation is being delivered in accordance with the first therapy program, a biomarker; and responsive to determining the biomarker satisfies a threshold, delivering, via the implantable device, electric stimulation to the patient in accordance with a second therapy program that is different than the first therapy program.

In another example, this disclosure describes a system includes cause the implantable device to deliver electric stimulation to a patient in accordance with a first therapy program; monitor, via the implantable device and while the electric stimulation is being delivered in accordance with the first therapy program, a biomarker; and responsive to determining the biomarker satisfies a threshold, cause the implantable device to deliver electric stimulation to the patient in accordance with a second therapy program.

In another example, this disclosure describes a computer readable medium includes cause an implantable device to deliver electric stimulation to a patient in accordance with a first therapy program; monitoring, via the implantable device and while the electric stimulation is being delivered in accordance with the first therapy program, a biomarker; and responsive to determining the biomarker satisfies a threshold, cause the implantable device to deliver electric stimulation to the patient in accordance with a second therapy program.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

DETAILED DESCRIPTION

Figure 1:
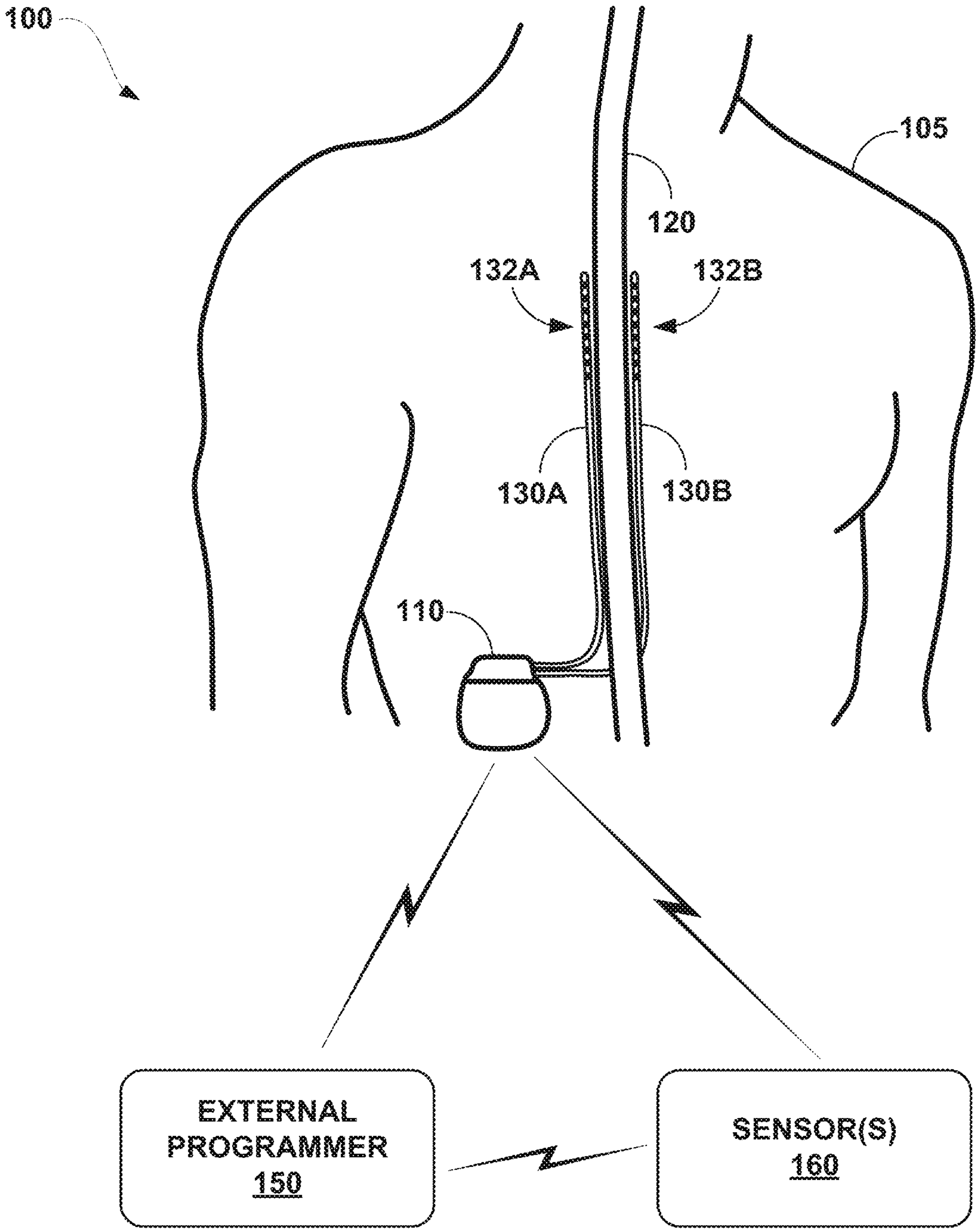
FIG. 1 is a conceptual diagram illustrating an example system that includes an implantable medical device (IMD) in the form of a neurostimulation device configured to deliver spinal cord stimulation (SCS), an external programmer, and one or more sensing devices in accordance with one or more techniques of this disclosure.

Stimulation therapy (e.g., including spinal cord stimulation, tibial nerve stimulation, etc.) may provide pain relief and/or other therapeutic benefits. In some circumstances, constant delivery of electrical stimulation doses may be required to achieve the desired pain relief and/or other therapeutic benefits. In other circumstances, electrical stimulation may have a durable effect such that constant delivery of electrical stimulation is not required to achieve the desired pain relief and/or other therapeutic benefits. Where electrical stimulation has such a durable effect, a device may deliver electrical stimulation to a patient in accordance with a treatment program that proscribes on-periods in which the device delivers electrical stimulation doses of the treatment program and off-periods in which the device does not deliver electrical stimulation doses of the treatment program.

In accordance with one or more techniques of this disclosure, a system may toggle between a plurality of electric stimulation programs, based the response of one or more monitored and/or measured biomarkers, to deliver electric stimulation to a patient via an implanted device. For example, an implanted device may deliver electric stimulation in accordance with a first therapy program, monitor a biomarker, and responsive to determining the biomarker satisfies a threshold, deliver electric stimulation to the patient in accordance with a second therapy program. In some examples, the one or more biomarkers may include a direct measure of patient symptoms, such as a patient's pain and/or pain score. In some example, the one or more biomarker may include other measures, such as an accelerometer measurement indicating a patient's movement and/or position, a pressure sensor, a physiological signal, a cardiac signal, a respiratory signal, a body temperature, a patient posture, a blood flow measurement, an evoked compound action potential (ECAP), and any other suitable biomarker suitable for determining the efficacy of electric stimulation.

In some examples, the first electric stimulation therapy program may be an "on" program comprising predetermined on-off times, electrodes, and parameters, and the second electric stimulation therapy program may be an "off" program, conserving power consumption and battery life of the implantable device and preventing over-stimulation of the patient. In other words, the system may determine that patient needs electric stimulation based on one or more biomarkers and deliver the stimulation accordingly, the system may subsequently determine that the patient no longer needs the electric stimulation based on one or more biomarkers and turn stimulation "off" and/or deliver electric stimulation in accordance with a "no stimulation" therapy program, and may then subsequently determine that the patient needs electric stimulation again based on one or more biomarkers and deliver electric stimulation again. In some examples, the system may determine which of a plurality of electric stimulation programs to deliver to the patient based on one or more biomarkers, e.g., different stimulation levels such as "high," "medium," "low," "off," and/or any other level and/or number of varying electric stimulation programs, and delivery the determined electric stimulation program accordingly.

FIG. 1 is a conceptual diagram illustrating an example system 100 that includes an implantable medical device (IMD) 110 configured to deliver spinal cord stimulation (SCS) therapy, processing circuitry 140, an external programmer 150, and one or more sensors 160, in accordance with one or more examples of this disclosure. Processing circuitry 140 may include one or more processors configured to perform various operations of IMD 110. Although the examples described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of electric stimulation, e.g., neurostimulation devices or other therapeutic applications of neurostimulation, including an external neurostimulator. For example, the system may not be a fully implanted system where the pulse generator is external to the patient and stimulation is transmitted transdermally. In one or more examples, the stimulators may be configured to deliver peripheral nerve stimulation or spinal nerve root stimulation.

As shown in FIG. 1, system 100 includes an IMD 110, leads 130A and 130B, and external programmer 150 shown in conjunction with a patient 105, who is ordinarily a human patient. In the example of FIG. 1, IMD 110 is an implantable electrical stimulator that is configured to generate and deliver electrical stimulation therapy to patient 105, e.g., for relief of chronic pain or other symptoms, via one or more electrodes 132A, 132B of leads 130A and/or 130B, respectively. In the example of FIG. 1, each lead 130A, 130B includes eight electrodes 132A, 132B respectively, although the leads may each have a different number of electrodes. Leads 130A, 130B may be referred to collectively as "leads 130" and electrodes 132A, 132B may be referred to collectively as "electrodes 132." In other examples, IMD 110 may be coupled to a single lead carrying multiple electrodes or more than two leads each carrying multiple electrodes.

IMD 110 may be a chronic electrical stimulator that remains implanted within patient 105 for weeks, months, or years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to one or more leads percutaneously implanted within the patient. In some examples, IMD 110 uses electrodes on one or more leads, while in other examples, IMD 110 may use one or more electrodes on a lead or leads and one of more electrodes on a housing of the IMD. In further examples, IMD 110 may be leadless and instead use only electrodes carried on a housing of the IMD.

IMD 110 may be constructed of any polymer, metal, or composite material sufficient to house the components of IMD 110 (e.g., components illustrated in FIGS. 2A, 2B) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted at other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

In the example of FIG. 1, electrical stimulation energy, which may be delivered as regulated current or regulated voltage-based pulses, is delivered from IMD 110 to one or more target tissue sites of patient 105 via leads 130 and electrodes 132. Leads 130 position electrodes 132 adjacent to target tissue of spinal cord 120. One or more of the electrodes 132 may be disposed at a distal tip of a lead 130 and/or at other positions at intermediate points along the lead. Leads 130 may be implanted and coupled to IMD 110. The electrodes 132 may transfer electrical stimulation generated by an electrical stimulation generator in IMD 110 to tissue of patient 105. Although leads 130 may each be a single lead, a lead 130 may include a lead extension or other segments that may aid in implantation or positioning of lead 130.

The electrodes 132 of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration. Deployment of electrodes via leads 130 is described for purposes of illustration, but electrodes may be arranged on a housing of IMD 110, e.g., in rows and/or columns (or other arrays or patterns), as surface electrodes, ring electrodes, or protrusions.

Neurostimulation stimulation parameters defining the electrical stimulation pulses delivered by IMD 110 through electrodes 132 of leads 130 may include information identifying which electrodes have been selected for delivery of the stimulation pulses according to a stimulation program and the polarities of the selected electrodes (the electrode combination), and voltage or current amplitude, pulse rate (i.e., frequency), and pulse width of the stimulation pulses. The neurostimulation stimulation parameters may further include a cycling parameter that specifies when, or how long, stimulation is turned on and off. Neurostimulation stimulation parameters may be programmed prior to delivery of the neurostimulation pulses, manually adjusted based on user input, or automatically controlled during delivery of the neurostimulation pulses, e.g., based on sensed conditions.

Although the example of FIG. 1 is directed to SCS therapy, e.g., to treat pain, in other examples, system 100 may be configured to treat other conditions that may benefit from neurostimulation therapy. For example, system 100 may be used to treat tremor, Parkinson's disease, epilepsy, or other neurological disorders, urinary or fecal incontinence, sexual dysfunction, obesity, or gastroparesis, or psychiatric disorders such as depression, mania, obsessive compulsive disorder, or anxiety disorders. Hence, in some examples, system 100 may be configured to deliver sacral neuromodulation (SNM), deep brain stimulation (DBS), peripheral nerve stimulation (PNS), or other stimulation, such as peripheral nerve field stimulation (PNFS), cortical stimulation (CS), gastrointestinal stimulation, or any other stimulation therapy capable of treating a condition of patient 105. In some examples, system 100 may be configured where the electrical stimulation includes stimulation parameters to deliver therapy to address a condition of one or more of painful diabetic neuropathy (PDN), peripheral vascular disease (PVD), peripheral artery disease (PAD), complex regional pain syndrome (CRPS), angina pectoris (AP), leg pain, back pain or pelvic pain.

Leads 130 may include, in some examples, one or more sensors configured to sense one or more physiological stimulation parameters of patient 105, such as patient activity, pressure, temperature, posture, heart rate, or other characteristics. At least some of electrodes 132 may be used to sense electrical signals within patient 105, additionally or alternatively to delivering stimulation. IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation. In some examples, the target tissue includes nerves, smooth muscle or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced into spinal cord 120 in via any suitable region, such as the thoracic, cervical or lumbar regions.

Stimulation of spinal cord 120 may, for example, prevent pain signals from being generated and/or traveling through spinal cord 120 and to the brain of patient 105. Patient 105 may perceive the interruption of pain signals as a reduction in pain and, therefore, efficacious therapy results. In some examples, stimulation of spinal cord 120 may produce paresthesia which may reduce the perception of pain by patient 105, and thus, provide efficacious therapy results. In other examples, stimulation of spinal cord 120 may be effective in reducing pain with or without presenting paresthesia. In some examples, some electrical stimulation pulses may be directed to glial cells while other electrical stimulation (e.g., delivered by a different electrode combination and/or with different stimulation parameters) is directed to neurons. In other examples, stimulation of spinal cord 120 may be effective in promoting blood flow in one or more remote tissue locations, e.g., in a limb or appendage, thereby alleviating or reducing pain or other symptoms, or preventing or delaying onset of tissue damage or degeneration.

IMD 110 generates and delivers electrical stimulation therapy to a target stimulation site within patient 105 via the electrodes of leads 130 to patient 105 according to one or more therapy stimulation programs. A therapy stimulation program specifies values for one or more stimulation parameters that define an aspect of the therapy delivered by IMD 110 according to that program. For example, a stimulation therapy program that controls delivery of stimulation by IMD 110 in the form of stimulation pulses may define values for voltage or current pulse amplitude, pulse width, and pulse rate (e.g., pulse frequency) for stimulation pulses delivered by IMD 110 according to that program, as well as the particular electrodes and electrode polarities forming an electrode combination used to deliver the stimulation pulses. Hence, a stimulation therapy program may specify the location(s) at which stimulation is delivered and amplitude, pulse width and pulse rate of the stimulation. In some examples, a stimulation therapy program may specify cycling of the stimulation, e.g., in terms of that when, or how long, stimulation is turned on and off.

A user, such as a clinician or patient 105, may interact with a user interface of an external programmer 150 to program IMD 110. Programming of IMD 110 may refer generally to the generation and transfer of commands, programs, or other information to control the operation of IMD 110. In this manner, IMD 110 may receive the transferred commands and programs from external programmer 150 to control electrical stimulation therapy. For example, external programmer 150 may transmit therapy stimulation programs, stimulation parameter adjustments, therapy stimulation program selections, user input, or other information to control the operation of IMD 110, e.g., by wireless telemetry or wired connection.

In some cases, external programmer 150 may be characterized as a physician or clinician programmer if it is primarily intended for use by a physician or clinician. In other cases, external programmer 150 may be characterized as a patient programmer if it is primarily intended for use by a patient. A patient programmer may be generally accessible to patient 105 and, in many cases, may be a portable device that may accompany patient 105 throughout the patient's daily routine, e.g., as a handheld computer similar to a tablet or smartphone. For example, a patient programmer may receive input from patient 105 when the patient wishes to terminate or change stimulation therapy. In general, a physician or clinician programmer may support selection and generation of programs by a clinician for use by IMD 110, and may take the form, for example, of a handheld computer (e.g., a tablet computer), laptop computer or desktop computer, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

IMD 110 and external programmer 150 may exchange information and may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 110 implant site to improve the quality or security of communication between IMD 110 and external programmer 150. Communication between external programmer 150 and IMD 110 may occur during power transmission or separate from power transmission.

IMD 110, in response to commands from external programmer 150, may deliver electrical stimulation therapy according to a plurality of therapy stimulation programs to a target tissue site of the spinal cord 120 of patient 105 via electrodes 132 on leads 130. In some examples, IMD 110 automatically modifies therapy stimulation programs as therapy needs of patient 105 evolve over time. For example, the modification of the therapy stimulation programs may cause the adjustment of at least one parameter of the plurality of stimulation pulses based on received information.

IMD 110 and/or external programmer 150 may receive information from one or more sensors 160, e.g., directly via wireless communication or indirectly from an intermediate server via a network connection. Sensor 160 may be positioned to sense one or more physiological responses at a selected location on patient 105. In some examples, sensor 160 may be positioned at, attached to or near tissue for a target anatomical area, e.g., at a limb or appendage, such as at or on a leg, toe, foot, arm, finger or hand of patient 105, e.g., to sense a galvanic skin response adjacent to placement of sensor 160. In some examples, sensor 160 may be attached to an appendage of the patient 105 to sense a physiological response associated with the appendage, e.g., by a clip-on mechanism, strap, elastic band and/or adhesive. In some examples, sensor 160 (or one of a plurality of sensors 160) may be implantable within patient 105, e.g., within a limb or appendage of the patient, near the spinal cord of the patient, within the brain of the patient, and the like.

In some examples, sensor 160 may be a physiological and/or patient posture or behavior sensor. For example, sensor 160 may be a heart rate monitor configured to detect and/or determine a heart rate and/or a heart rate variability. Sensor 160 may be configured to detect and/or determine a galvanic skin response, or to detect and/or determine a biopotential. Sensor 160 may be a thermometer configured to detect and/or determine a temperature of at least a part of the patient's anatomy. Sensor 160 may be configured to measure a pressure, e.g., a patient blood pressure, or to measure an impedance of at least a portion of the patient's anatomy. Sensor 160 may be a blood flow sensor that measures blood flow and provides information related to blood flow associated with tissue of the patient. For example, sensor 160 may provide blood flow values, or other information indicative of blood flow values or changes in blood flow values. The blood flow value may be an instantaneous blood flow measurement or may be a measurement of blood flow over a period of time such as average blood flow value, maximum blood flow value, minimum blood flow value during the period of time. In some examples, sensor 160 may be a microphone configured to detect/determine sounds of at least a portion of the patient's anatomy. In some examples, sensor 160 may at least partially comprise electrodes 132A, 132B. For example, sensor 160 may be configured to detect and/or determine ECAPs, local field potentials (LFPs), a network excitability, and the like. In some examples, sensor 160 may comprise and accelerometer configured to detect and/or determine a position and/or patient movement, a patient movement history over a predetermined amount of time, and the like. In some examples, sensor 160 may be a patient-input device, e.g., external programmer 150, a smartphone or computing device, or any other suitable device, configured to receive and communicate subjective patient feedback. For example, sensor 160 may be configured to receive a pain response, a pain score, an area of pain, an amount of paresthesia, an area of paresthesia, information relating to voiding and/or a voiding rate (e.g., voids per day), and the like. In some examples, sensor 160 may be an environmental sensor, such as a microphone, thermometer, hygrometer, pressure sensor, and the like, configured to detect and/or determine sounds, temperatures, humidity and pressure, etc., of the environment in which the patient is located.

In accordance with one or more aspects of this disclosure, system 100 and/or IMD 110 and/or external programmer 150 may be configured to control the delivery and/or parameters of electric stimulation based on one or more biomarkers. IMD 110 and/or external programmer 150 may be configured to deliver electric stimulation to a patient in accordance with a first therapy program, monitor a biomarker while electric stimulation is being delivered in accordance with the first therapy program, and deliver electric stimulation to the patient in accordance with a second therapy program responsive to determining that the biomarker satisfies a threshold. In some examples, the first therapy program may include a first amount of electric stimulation, the second therapy program may include a second amount of electric stimulation, and the second amount of electric stimulation is less than the first amount of electric stimulation. In some examples, the second amount of electric stimulation may be a zero amount of stimulation, e.g., the electric stimulation in accordance with the second therapy program may be "off" In this way, IMD 110 may be configured to consume and/or use less electrical power when delivering the maintenance dose relative to delivering the loading dose, and to have an increased battery life. Additionally or alternatively, IMD 110 may be configured to reduce eliminate, reduce, alleviate, or delay stimulation tolerance by delivering the first therapy program as needed, based on the biomarker, and reducing the amount of electric stimulation by delivering the second.

In some examples, IMD 110 and/or external programmer 150 may be configured to toggle back and forth between therapy programs. For example, IMD 110 and/or external programmer 150 may be configured to determine which of the first or second therapy programs to deliver based on one or more biomarkers and switch the delivery of electric stimulation between the first and second programs accordingly.

In some examples, IMD 110 and/or external programmer 150 may be configured to deliver one or more electric stimulation therapy programs based on one or more biomarkers, e.g., differing levels of stimulation based on the one or more biomarkers. For example, IMD 110 and/or external programmer 150 may be configured to deliver electric stimulation in accordance with a first therapy program including an amount of electric stimulation that is greater than the amount of electric stimulation that may be delivered in accordance with a second therapy program, which in turn may be an amount of electric stimulation that is greater than the amount of electric stimulation that may be delivered in accordance with a third therapy program, e.g., "high," "medium," and "low" electric stimulation programs. IMD 110 and/or external programmer 150 may determine which of the first, second, or third programs are to be delivered based on one or more biomarkers. In some examples, IMD 110 and/or external programmer 150 may toggle back and forth between any of multiple therapy programs based on one or more biomarkers.

Figure 2A:
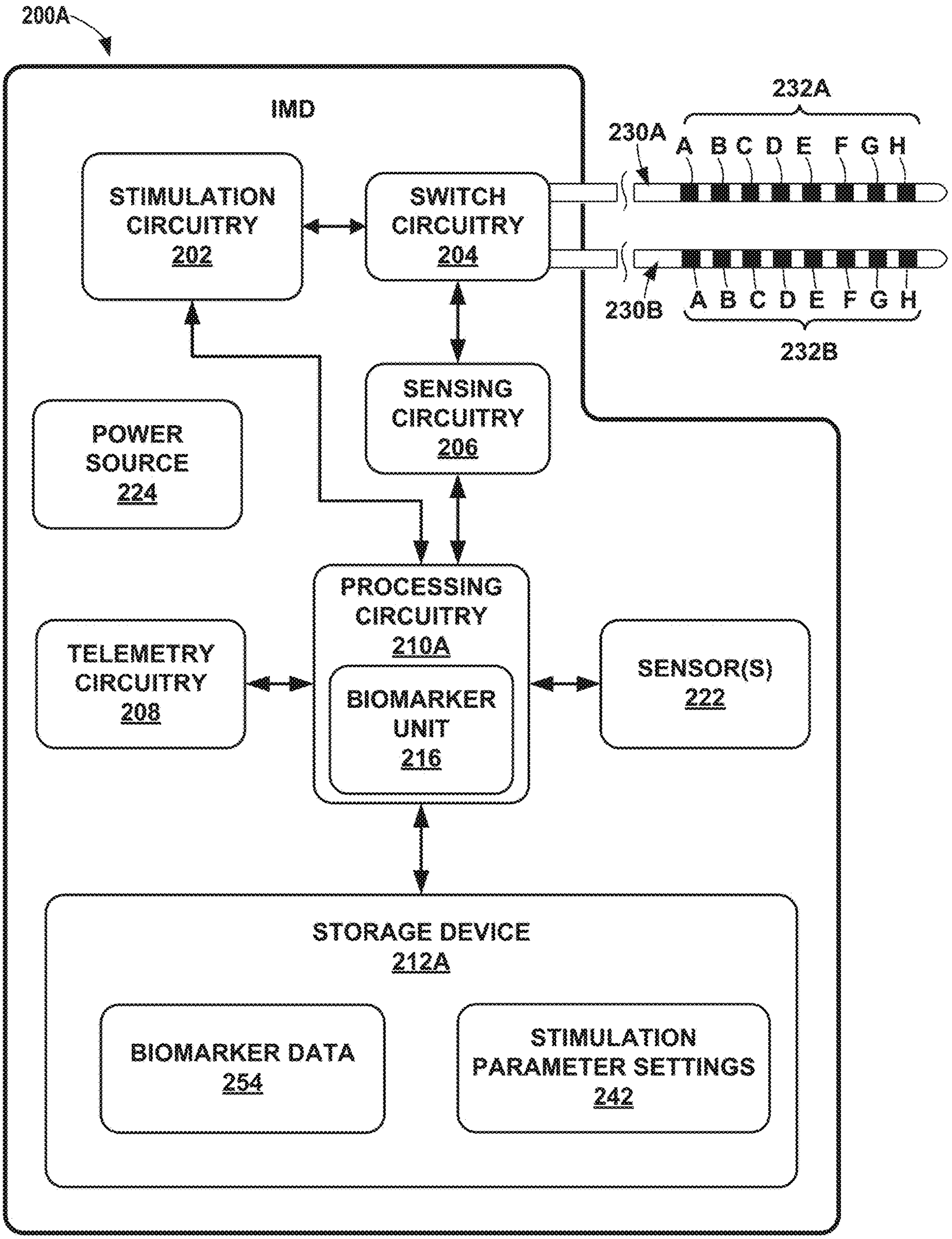
FIG. 2A is a block diagram illustrating an example of an IMD in the form of a neurostimulation device, in accordance with one or more techniques of this disclosure.
Figure 2B:
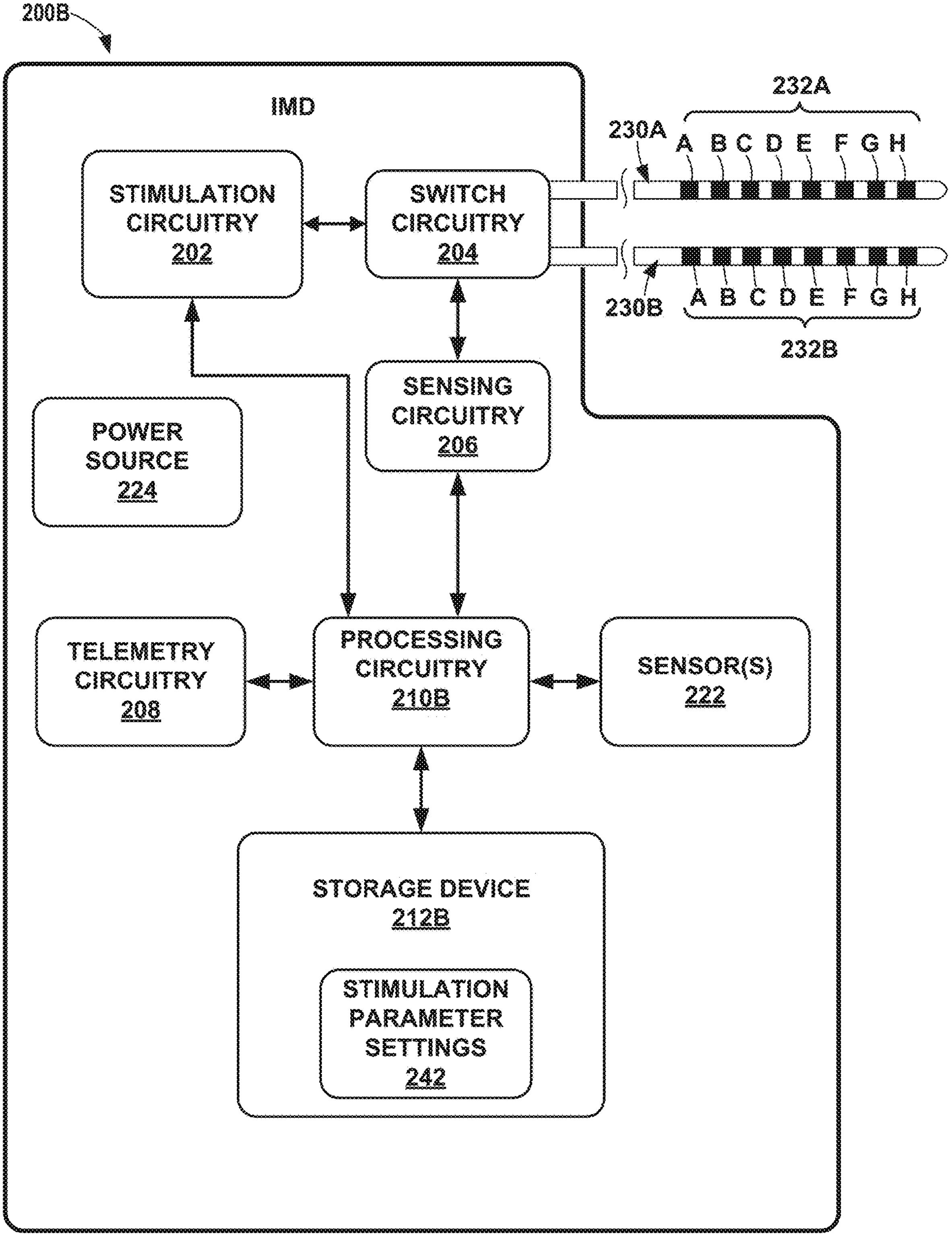
FIG. 2B is a block diagram illustrating an example of an IMD in the form of a neurostimulation device, in accordance with one or more techniques of this disclosure.

FIGS. 2A and 2B are block diagrams illustrating example configurations of components of an IMD 200A and an IMD 200B, respectively, in accordance with one or more techniques of this disclosure. IMD 200A and/or IMD 200B may be an example of IMD 110 of FIG. 1. In the examples shown in FIGS. 2A and 2B, IMD 200A and IMD 200B each include stimulation generation circuitry 202, switch circuitry 204, sensing circuitry 206, telemetry circuitry 208, sensor(s) 222, power source 224, lead 230A carrying electrodes 232A, which may correspond to lead 130A and electrodes 132A of FIG. 1, and lead 230B carrying electrodes 232B, which may correspond to lead 130B and electrodes 132B of FIG. 1. In the examples shown in FIG. 2A, IMD 200A includes processing circuitry 210A and storage device 212A, and in the example shown in FIG. 2B, IMD 200B includes processing circuitry 210B and storage device 212B. Processing circuitry 210A and/or 210B may include one or more processors configured to perform various operations of IMD 200A and/or IMD 200B.

In the examples shown in FIGS. 2A and 2B, storage devices 212A and 212B store stimulation parameter settings 242. In addition, as shown in FIG. 2A, storage device 212A may store biomarker data 254 obtained directly or indirectly from one or more sensors 222, which may correspond to sensors 160 of FIG. 1 or from a patient, e.g., patient 105, via a patient-input device. In this case, IMD 200A of FIG. 2A may process biomarker data and select or adjust stimulation parameter settings, including cycling, based on the biomarker data.

In some examples, biomarker data 254 includes data and/or information from one or more sensors 222 and/or 160, patient provided information such as a pain level via a patient-input device, and/or any other information and/or data indicative of a current state of the patient or indicative of a response of the patient to electric stimulation. Biomarker data 254 may include galvanic skin response data such as a voltage or conductance. Biomarker data 254 may include measured and/or sensed electrochemical activity and biopotentials. Biomarker data 254 may include a temperature, a pressure, a blood pressure, a blood flow, an impedance, sounds and/or audio data, ECAPs, LFPs, a network excitability, accelerometer data and/or a patient position, posture, or movement, and the like.

In one or more examples, such as shown in FIG. 2B, the IMD 200B may not store or receive the biomarker data. Instead, external programmer 150 or another device may directly or indirectly select or adjust stimulation parameter settings based on biomarker data and communicate the selected settings or adjustments to IMD 200B of FIG. 2B. In some examples, stimulation parameter settings 242 may include stimulation parameters (sometimes referred to as "sets of therapy stimulation parameters") for respective different stimulation programs selectable by the clinician or patient for therapy. In some examples, stimulation parameter settings 242 may include one or more recommended parameter settings. In this manner, each stored therapy stimulation program, or set of stimulation parameters, of stimulation parameter settings 242 defines values for a set of electrical stimulation parameters (e.g., a stimulation parameter set), such as electrode combination (selected electrodes and polarities), stimulation current or voltage amplitude, stimulation pulse width, pulse rate, and/or duty cycle. In some examples, stimulation parameter settings 242 may further include cycling information indicating when or how long stimulation is turned on and off, e.g., periodically and/or according to a schedule. For example, recommended parameter settings may indicate the stimulation to turn on for a certain period of time, and/or to turn off stimulation for a certain period of time. In another example, recommended cycle parameter settings may indicate for stimulation to turn on for a period of time without creating desensitization of the stimulation. In one or more examples, the recommended parameter settings may indicate stimulation to occur at a certain time of day, for example when the patient is typically awake or active, or sleeping. In one or more examples, recommended parameter settings relate to when the patient has a certain posture, for example only deliver stimulation when the patient is in a supine position.

Stimulation generation circuitry 202 includes electrical stimulation circuitry configured to generate electrical stimulation and generates electrical stimulation pulses selected to alleviate symptoms of one or more diseases, disorders or syndromes. While stimulation pulses are described, stimulation signals may take other forms, such as continuous-time signals (e.g., sine waves) or the like. The electrical stimulation circuitry may reside in an implantable housing, for example of the IMD. Each of leads 230A, 230B may include any number of electrodes 232A, 232B. The electrodes are configured to deliver the electrical stimulation to the patient. In the example of FIGS. 2A and 2B, each set of electrodes 232A, 232B includes eight electrodes A-H. In some examples, the electrodes are arranged in bipolar combinations. A bipolar electrode combination may use electrodes carried by the same lead 230A, 230B or different leads. For example, an electrode A of electrodes 232A may be a cathode and an electrode B of electrodes 232A may be an anode, forming a bipolar combination. Switch circuitry 204 may include one or more switch arrays, one or more multiplexers, one or more switches (e.g., a switch matrix or other collection of switches), or other electrical circuitry configured to direct stimulation signals from stimulation generation circuitry 202 to one or more of electrodes 232A, 232B, or directed sensed signals from one or more of electrodes 232A, 232B to sensing circuitry 206. In some examples, each of the electrodes 232A, 232B may be associated with respective regulated current source and sink circuitry to selectively and independently configure the electrode to be a regulated cathode or anode. Stimulation generation circuitry 202 and/or sensing circuitry 206 also may include sensing circuitry to direct electrical signals sensed at one or more of electrodes 232A, 232B.

Sensing circuitry 206 may be configured to monitor signals from any combination of electrodes 232A, 232B. In some examples, sensing circuitry 206 includes one or more amplifiers, filters, and analog-to-digital converters. Sensing circuitry 206 may be used to sense physiological signals, such as ECAP signals and/or LFP signals. In some examples, sensing circuitry 206 detects ECAP and/or LFP signals from a particular combination of electrodes 232A, 232B. In some cases, the particular combination of electrodes for sensing ECAP and/or LFP signals includes different electrodes than a set of electrodes 232A, 232B used to deliver stimulation pulses. Alternatively, in other cases, the particular combination of electrodes used for sensing ECAP and/or LFP signals includes at least one of the same electrodes as a set of electrodes used to deliver stimulation pulses to patient 105. Sensing circuitry 206 may provide signals to an analog-to-digital converter, for conversion into a digital signal for processing, analysis, storage, or output by processing circuitry 210.

Telemetry circuitry 208 supports wireless communication between IMD 200A and/or IMD 200B and an external programmer or another computing device under the control of processing circuitry 210. Processing circuitry 210A and/or 210B of IMD 200A and/or IMD 200B, respectively, may receive, as updates to programs, values for various stimulation parameters such as amplitude and electrode combination, from the external programmer via telemetry circuitry 208. Processing circuitry 210A and/or 210B of IMD 200A and/or IMD 200B, respectively, may store updates to the stimulation parameter settings 242 or any other data in storage device 212A and/or 212B. Telemetry circuitry 208 in IMD 200A and/or IMD 200B, as well as telemetry circuits in other devices and systems described herein, such as the external programmer and patient feedback sensing system, may accomplish communication by radiofrequency (RF) communication techniques. In addition, telemetry circuitry 208 may communicate with an external medical device programmer via proximal inductive interaction of IMD 200A and/or IMD 200B with the external programmer, where the external programmer may be one example of external programmer 150 of FIG. 1. Accordingly, telemetry circuitry 208 may send information to the external programmer on a continuous basis, at periodic intervals, or upon request from IMD 110 or the external programmer.

Processing circuitry 210A and/or 210B may include one or more processors, such as any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210A and/or 210B herein may be embodied as firmware, hardware, software or any combination thereof. Processing circuitry 210A and/or 210B controls stimulation generation circuitry 202 to generate stimulation signals according to stimulation parameter settings 242. In some examples, processing circuitry 210A and/or 210B may execute other instructions stored in storage device 212A and/or 212B, respectively, to apply stimulation parameters specified by one or more of programs, such as amplitude, pulse width, pulse rate, and pulse shape of each of the stimulation signals.

In the illustrated example of FIG. 2A, processing circuitry 210A includes a biomarker unit 216 to process biomarker data. Biomarker unit 216 may represent an example of a portion of processing circuitry configured to process biomarker data received from a sensor, such as sensors 222 and/or 160, and/or a patient-input device, such as external programmer 150 or a patient device such as the patient's phone and/or computing device. In the example of FIG. 2B, the processing of biomarker data occurs in a device other than IMD 200B. Referring again to FIG. 2A, the biomarker unit 216, discussed further below, receives information regarding the biomarker data, such as information relating to sensed and/or received biomarkers and/or patient feedback associated with the efficacy of the electrical stimulation therapy, and controls the electrical stimulation circuitry 202 to deliver the electrical stimulation to the patient based on the received information, where the received information may be stored in a storage device. Processing circuitry 210A and/or 210B also controls stimulation generation circuitry 202 to generate and apply the stimulation signals to selected combinations of electrodes 232A, 232B. In some examples, stimulation generation circuitry 202 includes a switch circuit (instead of, or in addition to, switch circuitry 204) that may couple stimulation signals to selected conductors within leads 230, which, in turn, deliver the stimulation signals across selected electrodes 232A, 232B. Such a switch circuit may selectively couple stimulation energy to selected electrodes 232A, 232B and to selectively sense bioelectrical neural signals of a spinal cord of the patient with selected electrodes 232A, 232B. In other examples, however, stimulation generation circuitry 202 does not include a switch circuit and switch circuitry 204 does not interface between stimulation generation circuitry 202 and electrodes 232A, 232B. In these examples, stimulation generation circuitry 202 may include a plurality of pairs of current sources and current sinks, each connected to a respective electrode of electrodes 232A, 232B. In other words, in these examples, each of electrodes 232A, 232B is independently controlled via its own stimulation circuit (e.g., via a combination of a regulated current source and sink), as opposed to switching stimulation signals between different electrodes of electrodes 232A, 232B.

Storage device 212A and/or 212B may be configured to store information within IMD 200A and/or 200B, respectively, during operation. Storage device 212A and/or 212B may include a computer-readable storage medium or computer-readable storage device. In some examples, storage device 212A and/or 212B includes one or more of a short-term memory or a long-term memory. Storage device 212A and/or 212B may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, storage device 212A and/or 212B is used to store data indicative of instructions, e.g., for execution by processing circuitry 210A and/or 210B, respectively. As discussed above, storage device 212A and/or 212B is configured to store stimulation parameter settings 242.

Power source 224 may be configured to deliver operating power to the components of IMD 200A and/or 200B. Power source 224 may include a battery and a power generation circuit to produce the operating power. In some examples, the battery is rechargeable to allow extended operation. In some examples, recharging is accomplished through proximal inductive interaction between an external charger and an inductive charging coil within IMD 200A and/or 200B. Power source 224 may include any one or more of a plurality of different battery types, such as nickel cadmium batteries and lithium ion batteries.

In some examples as shown in FIG. 2A, the processing circuitry 210A of the IMD 200A directs delivery of electrical stimulation by the electrodes 232A, 232B of leads 230A, 230B, receives biomarker data 254 from sensors 222 or a patient-input device, stores biomarker data 254 in storage device 212A, and generates output based on the received biomarker data 254 and/or information. For example, biomarker unit 216 may receive biomarker data 254 in response to delivery of electrical stimulation by the electrodes 232A, 232B. In other examples, biomarker unit 216 may receive biomarker data 254 when electrical stimulation is not delivered, e.g., biomarker data 254 that is not in response to electrical stimulation or has a delayed response and/or durable effect (e.g., relatively long-lasting) response to electrical stimulation. In some examples, biomarker unit 1 may use biomarker data 254 to develop recommended electrical stimulation parameters or adjustments which are outputted to a user, and the user can use the indications or one or more recommended stimulation parameters to program the IMD 200A, e.g., by selecting or accepting the recommendations as stimulation parameter settings to be used by IMD 200A. For example, a particular cycling, electrode combination, and/or a set of stimulation parameters may be recommended to a user and presented to the user via the programmer as a therapy program. The user may accept the recommended therapy program, and the programmer programs IMD 200A to implement and deliver stimulation with the selected therapy program.

In some examples, the biomarker unit 216 may use biomarker data 254 to perform closed-loop control of the stimulation parameters. For example, patient feedback unit 216 may select or adjust one or more electric stimulation settings and/or parameter values, such as electrode combination, amplitude, pulse width or pulse rate, or cycling in response to patient feedback information, based on biomarker data 254.

In some examples, the processing circuitry 210A and/or 210B of the IMD 200A and/or 200B, respectively, directs delivery of electrical stimulation of the electrodes 232A, 232B, and receives biomarker data 254 from one or more sensors 160 and/or sensors 222 either directly (e.g., in the case of processing circuitry 210A) or via external controller (e.g., in the case of processing circuitry 210B), and controls the delivery of electrical stimulation of the electrodes 232A, 232B based on the received biomarker data 254. Biomarker data 254 may be received via the telemetry circuitry 208 either directly or indirectly from sensors 160 and/or sensors 222 In an example, the IMD 200A and/or IMD 200B may receive biomarker data from an intermediate device other than the patient feedback sensor, such as external programmer 150.

Figure 3:
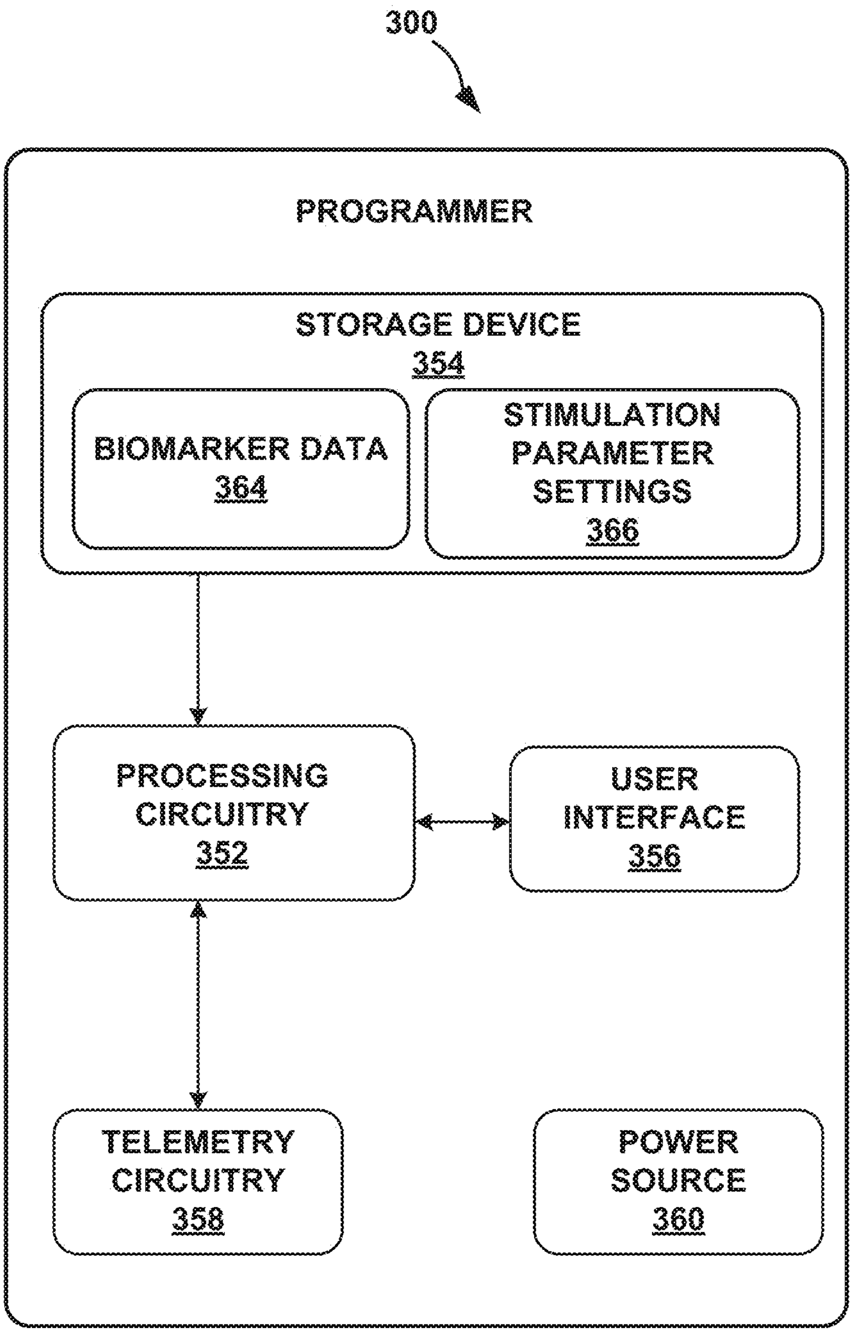
FIG. 3 is a block diagram illustrating an example of an external programmer suitable for use with the IMD of FIG. 2, in accordance with one or more techniques of this disclosure.

FIG. 3 is a block diagram illustrating an example configuration of components of an example external programmer 300. External programmer 300 may be an example of external programmer 150 of FIG. 1. Although external programmer 300 may generally be described as a hand-held device, such as a tablet computer or smartphone-like device, external programmer 300 may be a larger portable device, such as a laptop computer, or a more stationary device, such as a desktop computer. In addition, in other examples, external programmer 300 may be included as part of an external charging device or include the functionality of an external charging device, e.g., to recharge a battery or batteries associated with an IMD, e.g., any of IMDs 110, 200A, or 200B described above. For brevity, external programmer 300 will be described with reference to IMD 200B, and it is to be understood that external 300 may be used with any of IMDs 110, 200A, 200B, or any other suitable IMD. As illustrated in FIG. 3, external programmer 300 may include processing circuitry 352, storage device 354, user interface 356, telemetry circuitry 358, and power source 360. In some examples, storage device 354 may store instructions that, when executed by processing circuitry 352, cause processing circuitry 352 and external programmer 300 to provide the functionality ascribed to external programmer 300 throughout this disclosure. Each of these components, circuitry, or modules, may include electrical circuitry that is configured to perform some, or all of the functionality described herein. For example, processing circuitry 352 may include processing circuitry configured to perform the processes discussed with respect to processing circuitry 352.

In general, external programmer 300 includes any suitable arrangement of hardware, alone or in combination with software and/or firmware, to perform the techniques attributed to external programmer 300, and processing circuitry 352, user interface 356, and telemetry circuitry 358 of external programmer 300. In various examples, processing circuitry 352, telemetry circuitry 358, or other circuitry of external programmer 300 may include one or more processors, such as one or more microprocessors, DSPs, ASICs, FPGAs, or any other equivalent integrated or discrete logic circuitry, as well as any combinations of such components. External programmer 300 also, in various examples, may include a storage device 354, such as RAM, ROM, PROM, EPROM, EEPROM, flash memory, a hard disk, a CD-ROM, including executable instructions for causing the one or more processors to perform the actions attributed to them. Moreover, although processing circuitry 352 and telemetry circuitry 358 are described as separate modules, in some examples, processing circuitry 352 and telemetry circuitry 358 are functionally integrated. In some examples, processing circuitry 352, telemetry circuitry 358 or other circuitry of external programmer 300 may correspond to individual hardware units, such as ASICs, DSPs, FPGAs, or other hardware units.

The processing circuitry 352 is configured to direct delivery of electrical stimulation and receive biomarker data 364. In some examples, the processing circuitry 352 is configured to control the electrical stimulation circuitry to deliver the electrical stimulation based on biomarker data 364 in a closed loop manner by directing the IMD 200B to use particular stimulation parameters.

Storage device 354 (e.g., a storage device) may, in some examples, store instructions that, when executed by processing circuitry 352, cause processing circuitry 352 and external programmer 300 to provide the functionality ascribed to external programmer 300 throughout this disclosure. For example, storage device 354 may include instructions that cause processing circuitry 352 to obtain a parameter set from memory or receive user input and send a corresponding command to IMD 200B, or instructions for any other functionality. In addition, storage device 354 may include a plurality of programs, where each program includes a parameter set that defines therapy stimulation or control stimulation. Storage device 354 may also store data received from a medical device (e.g., IMD 200B) and/or a remote sensing device. For example, storage device 354 may store data recorded at a sensing module of the medical device, and storage device 354 may also store data from one or more sensors of the medical device. In an example, storage device 354 may store data recorded at a remote sensing device such as biomarker data 364 from one or more sensors and/or patient-input devices.

User interface 356 may include a button or keypad, lights, a speaker for voice commands, a display, such as a liquid crystal (LCD), light-emitting diode (LED), or organic light-emitting diode (OLED). In some examples, the display includes a touch screen. User interface 356 may be configured to display any information related to the delivery of electrical stimulation including output, for example, based on the patient feedback information. User interface 356 may also receive user input (e.g., indication of when the patient perceives stimulation, or a pain score perceived by the patient upon delivery of stimulation) via user interface 356. The user input may be, for example, in the form of pressing a button on a keypad or selecting an icon from a touch screen. The input may request starting or stopping electrical stimulation, the input may request a new electrode combination or a change to an existing electrode combination, or the input may request some other change to the delivery of electrical stimulation, such as a change in stimulation cycling amplitude, pulse width or pulse rate.

Telemetry circuitry 358 may support wireless communication between the medical device and external programmer 300 under the control of processing circuitry 352. Telemetry circuitry 358 may also be configured to communicate with another computing device via wireless communication techniques, or direct communication through a wired connection. In some examples, telemetry circuitry 358 provides wireless communication via an RF or proximal inductive medium. In some examples, telemetry circuitry 358 includes an antenna, which may take on a variety of forms, such as an internal or external antenna.

Examples of local wireless communication techniques that may be employed to facilitate communication between external programmer 300 and IMD 200B include RF communication according to the 802.11 or Bluetooth® specification sets or other standard or proprietary telemetry protocols. In this manner, other external devices may be capable of communicating with external programmer 300 without needing to establish a secure wireless connection. As described herein, telemetry circuitry 358 may be configured to transmit a spatial electrode movement pattern or other stimulation parameters to IMD 200B for delivery of electrical stimulation therapy.

Power source 360 is configured to deliver operating power to the components of external programmer 300. Power source 360 may include a battery and a power generation circuit to produce the operating power. In some examples, the battery is rechargeable to allow extended operation. Recharging may be accomplished by electrically coupling power source 360 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an alternating current outlet to operate.

In some examples, the external programmer 300 or an external control device directs delivery of electrical stimulation of an IMD, receives biomarker data 364, and generates output based on the received data, e.g., for evaluation of efficacy of stimulation parameters, determine one or more therapy programs to be delivered, and/or to recommend or assist a user in programming stimulation parameters for delivery of electrical stimulation, or used as part of a closed loop control device to automatically adjust stimulation parameters using biomarker data 364.

Programmer 300 may be a patient programmer or a clinician programmer and receives biomarker data such as biomarker data 364. Programmer 300 receives biomarker data and allows a user to interact with the processing circuitry 352 via user interface 356 in order to select a therapy program or identify efficacious parameter settings, such as cycling and/or one or more other stimulation parameters using the biomarker data. Programmer 300 further assists the user in programming a neurostimulation device by using the biomarker data displayed on the user interface 356. In addition, programmer 300 may be used as part of a closed loop control device to automatically adjust stimulation parameters based at least on biomarker data. In some examples, programmer 300 receives biomarker data such as biomarker data 364 from the patient feedback device and stores the biomarker data in the storage device 354.

In an example, programmer 300 may be used to cause the IMD to automatically select a therapy program. Processing circuitry 352 causes the IMD to automatically scan through each of a plurality of parameter combinations, including electrode combinations and parameter combinations, and/or one or more predetermined therapy programs, e.g., in response to received biomarker data 364.

The architecture of external programmer 300 illustrated in FIG. 3 is shown as an example. The techniques as set forth in this disclosure may be implemented in the example external programmer 300 of FIG. 3, as well as other types of systems not described specifically herein. Nothing in this disclosure should be construed so as to limit the techniques of this disclosure to the example architecture illustrated by FIG. 3.

Figure 4:
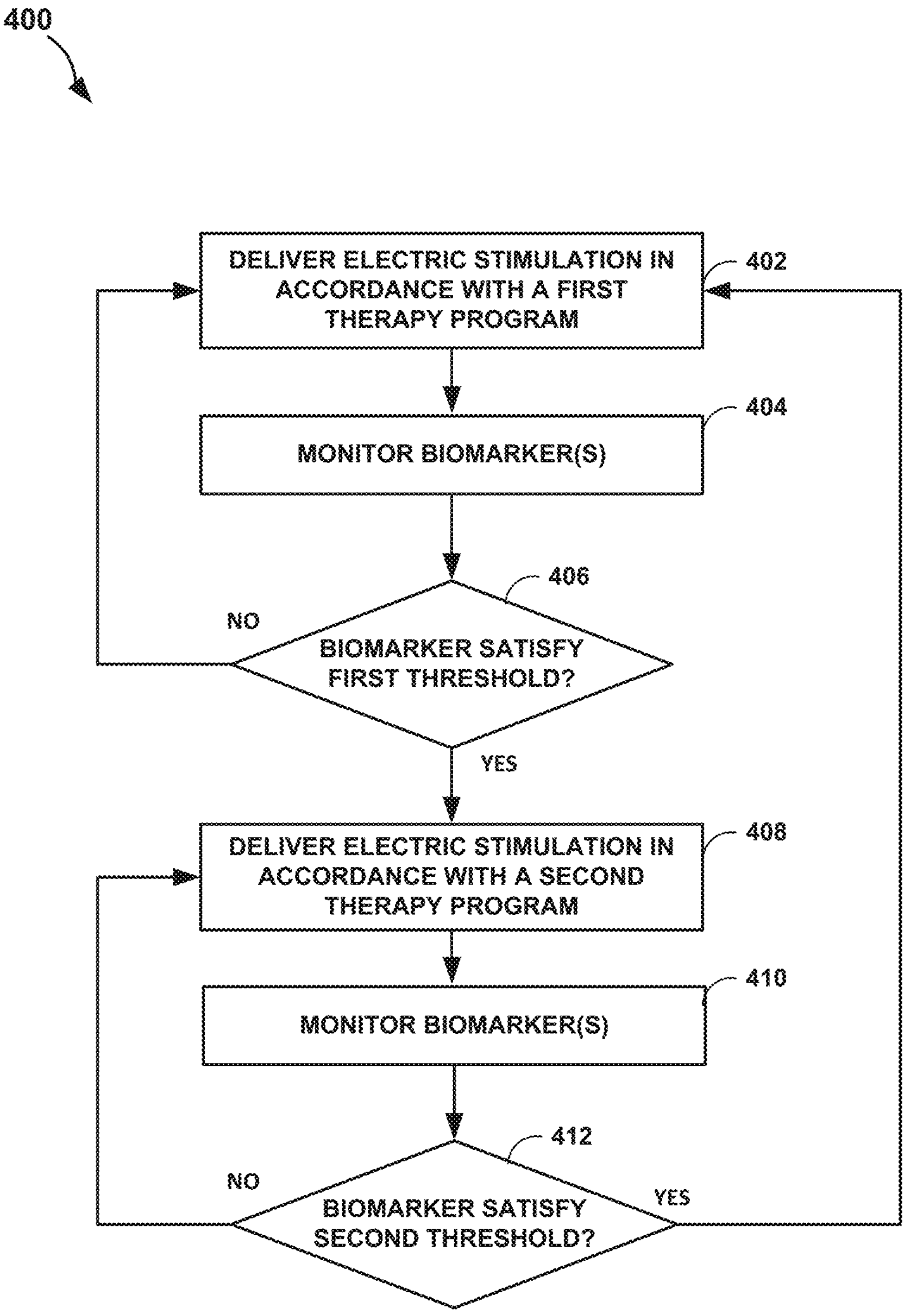
FIG. 4 is a flow diagram illustrating an example method of controlling electric stimulation, in accordance with one or more techniques of this disclosure.

FIG. 4 is a flow diagram illustrating an example method 400 of controlling electric stimulation, in accordance with one or more techniques of this disclosure. Although FIG. 4 is discussed using IMD 200A and/or IMD 200B of FIGS. 2A and 2B and external programmer 300 of FIG. 3, it is to be understood that the methods discussed herein may include and/or utilize other systems and methods in other examples.

IMD 200A may deliver electric stimulation to a patient in accordance with a first therapy program (402). For example, the first therapy program may include one or more programmable stimulation parameter settings defining the electrical stimulation therapy to be delivered by the IMD 200A to the patient, e.g., stimulation parameter settings 242. In some examples, the first therapy program may be a therapy program including a first amount of electric stimulation therapy, e.g., a first amount of any of an amplitude, frequency, pulse width, and cycling of the electric stimulation. In some examples, the first therapy program may include electric stimulation comprising a frequency of at least 10 kilohertz (kHz).

IMD 200A may monitor a biomarker (404). In some examples, IMD 200A monitor one or more biomarkers while electric stimulation is being delivered in accordance with the first therapy program. In other examples, IMD 200A monitor one or more biomarkers after electric stimulation was delivered in accordance with the first therapy program, e.g., the one or more biomarkers may have a delayed response and/or a long-lasting response or response according to a durable effect. For example, processing circuitry 210A may control stimulation circuitry 202 to deliver stimulation energy via electrodes 232A, 232B with stimulation parameters specified by one or more stimulation parameter settings 242 stored on storage device and defined by the first therapy program, and sensors 222 and/or an external device such as a patient-input device may sense and/or measure a response, e.g. biomarker data, to the delivered electric stimulation. Processing circuitry 210A may then receive the biomarker data from sensors 222 and/or other device, e.g., via telemetry circuitry 208, store biomarker data, e.g., biomarker data 254, in storage device 212A, and process the biomarker data.

In some examples, the biomarker may be at least one of a direct measure of patient symptoms, patient input, an accelerometer and/or accelerometer data, a pressure sensor and/or pressure data, a physiological signal, a cardiac signal, a heart rate, a heart rate variability, a signal and/or information related to a circadian rhythm, a blood flow, a respiratory signal, a body temperature, one or more LFPs, one or more ECAPs, a network excitability, a galvanic skin response, or any suitable biomarker for determining the efficacy of the first therapy program. For example, the biomarker may be a pain response, a pain score, an area of pain, an amount of paresthesia, an area of paresthesia, a signal and/or information relating to voiding and/or a voiding rate (e.g., voids per day), and the like. In some examples, the biomarker may be a patient posture and/or patient behavior data such as patient position, patient movement, patient movement history over a predetermined amount of time, a history of patent-selected stimulation parameters over a predetermined amount of time, and the like.

IMD 200A may determine that the biomarker, e.g., the biomarker data 254 generated by the biomarker in response to the delivered electric stimulation, satisfies a first threshold, e.g., the YES branch at (406). For example, the biomarker may be a pain level and/or score input by the patient, and the pain level and/or score may be equal to or less than a first threshold value indicating that the electric stimulation therapy is no longer needed. In another example, the biomarker may be an ECAP signal including a signal feature (e.g., a frequency, a peak, a valley, a duration, an integrated value over time, and the like) which may satisfy a first threshold pertaining to the feature by its presence and/or value, indicating that the therapy is no longer needed and/or would be beneficial. In some examples, IMD 200A may determine that the biomarker does not satisfy the first threshold, e.g., the NO branch at (406), and IMD 200A may then continue to deliver electric stimulation in accordance with the first therapy program.

IMD 200A may deliver electric stimulation to a patient in accordance with a second therapy program (408), e.g., responsive to determining that the biomarker satisfies the threshold. In some examples, the second therapy program may comprise not delivering electric stimulation, e.g., an "off" or "zero" stimulation program. In some examples, electric stimulation delivered in accordance with the second therapy program is an amount of electric stimulation that is less than the amount of electric stimulation delivered in accordance with the first therapy program. In some examples, the second therapy program may include electric stimulation comprising a frequency of at least 10 kilohertz (kHz). In some examples, IMD 200A may deliver electric stimulation according to the second therapy program that is sufficient for capturing an ECAP and/or ECAP signal, e.g., the second therapy program is capable of evoking an ECAP signal which sensors 222 may detect, sense, measure, or otherwise capture.

IMD 200A may monitor a biomarker (410), e.g., during or after delivering of the electric stimulation in accordance with the second therapy program. In some examples, the biomarker may be one or more second biomarkers that are different from the one or more first biomarkers, e.g., one or more first biomarkers monitored during or after delivery of electric stimulation according to the first therapy program at (404). In some examples, the second biomarker(s) may be the same as the first biomarkers(s).

In some examples, processing circuitry 210A may control stimulation circuitry 202 to deliver stimulation energy via electrodes 232A, 232B with stimulation parameters specified by one or more stimulation parameter settings 242 stored on storage device and defined by the second therapy program, and sensors 222 and/or an external device such as a patient-input device may sense and/or measure a response, e.g. second biomarker data, to the delivered electric stimulation. Processing circuitry 210A may then receive the second biomarker data from sensors 222 and/or other device, e.g., via telemetry circuitry 208, store the second biomarker data, e.g., as biomarker data 254, in storage device 212A, and process the second biomarker data.

IMD 200A may deliver one or more electric stimulation maintenance doses to the patient according to the maintenance dose stimulation parameters for a second time period (410). For example, processing circuitry 210A may control stimulation circuitry 202 to deliver stimulation energy via electrodes 232A, 232B with stimulation parameters specified by one or more stimulation parameter settings 242 stored on storage device, such as the determined maintenance dose. In some examples, IMD 200A may deliver one or more electric stimulation maintenance doses that consume less power of IMD 200A than the loading dose.

In some examples, the second biomarker may be at least one of a direct measure of patient symptoms, patient input, an accelerometer and/or accelerometer data, a pressure sensor and/or pressure data, a physiological signal, a cardiac signal, a heart rate, a heart rate variability, a signal and/or information related to a circadian rhythm, a blood flow, a respiratory signal, a body temperature, one or more LFPs, one or more ECAPs, a network excitability, a galvanic skin response, or any suitable biomarker for determining the efficacy of the first therapy program. For example, the second biomarker may be a pain response, a pain score, an area of pain, an amount of paresthesia, an area of paresthesia, a signal and/or information relating to voiding and/or a voiding rate (e.g., voids per day), and the like. In some examples, the second biomarker may be a patient posture and/or patient behavior data such as patient position, patient movement, patient movement history over a predetermined amount of time, a history of patent-selected stimulation parameters over a predetermined amount of time, and the like.

IMD 200A may determine that the second biomarker, e.g., generated in response to the delivered electric stimulation in accordance with the second therapy program, satisfies a second threshold, e.g., the YES branch at (412). For example, the second biomarker may be a pain level and/or score input by the patient, and the pain level and/or score may be equal to or greater than a second threshold value indicating that more electric stimulation therapy is needed. In another example, the second biomarker may be an ECAP signal including a signal feature (e.g., a frequency, a peak, a valley, a duration, an integrated value over time, and the like) which may satisfy a second threshold pertaining to the feature by its presence and/or value, indicating that more therapy is needed and/or would be beneficial. In some examples, IMD 200A may determine that the second biomarker does not satisfy the second threshold, e.g., the NO branch at (412), and IMD 200A may then continue to deliver electric stimulation in accordance with the second therapy program.

In some examples, the first threshold and the second threshold may be the same threshold and threshold value pertaining to the same biomarker, e.g., the first and second biomarkers at (404) and (410) may be the same and the first and second thresholds may be the same. For example, the biomarker "crossing" the threshold in a first direction, from greater to lesser or vice versa, satisfies the first threshold and IMD 200A proceeds to deliver electric stimulation in accordance with the second therapy program as at (408), and the biomarker crossing the threshold in the other direction, from lesser to greater or vice versa, satisfies the second threshold and IMD 200A proceeds to deliver electric stimulation in accordance with the first therapy program as at (402).

In some examples, the first threshold and the second threshold may be different from each other and pertain to the same biomarker. For example, there may be a set of biomarker values between the first and second thresholds for which either the first or second therapy programs may be delivered depending on which therapy program is currently being delivered, or method 200 may include hysteresis. For example, the first threshold may be a first pain score and the second threshold may be a second pain score that is greater than the first pain score. As an illustrative example, the first threshold may be a pain score of 4 on a scale from 1 to 10, and the second threshold may be a pain score of 6. IMD 200A may deliver electric stimulation according to the first therapy program (402), monitor the biomarker (404), and switch to delivering the electric stimulation in accordance with the second therapy program (408) if the pain score satisfies the first threshold, e.g., is equal to or less than 4 (406). IMD 200A may subsequently deliver electric stimulation according to the second therapy program (408), monitor the biomarker (410), and switch to delivering the electric stimulation in accordance with the first therapy program (402) if the pain score satisfies the second threshold, e.g., is equal to or greater than 6 (4012).

In some examples, the first threshold and the second threshold may be different from each other and pertain to different biomarkers. For example, the first biomarker may be an ECAP for which the first threshold is a particular ECAP signal feature, and the second biomarker for which the second threshold may be a pain score of a particular value.

In some examples, IMD 200A may toggle between delivering electric stimulation in accordance with the first and second programs within seconds, e.g., in less than 10 seconds. For example, method steps (402)-(412) may occur in less than 10 seconds. In other examples, method steps (402)-(412) may occur over the course of several hours, e.g., 2 hours, 10 hours, 24 hours, or over the course of one or more days, or longer.

Figure 5:
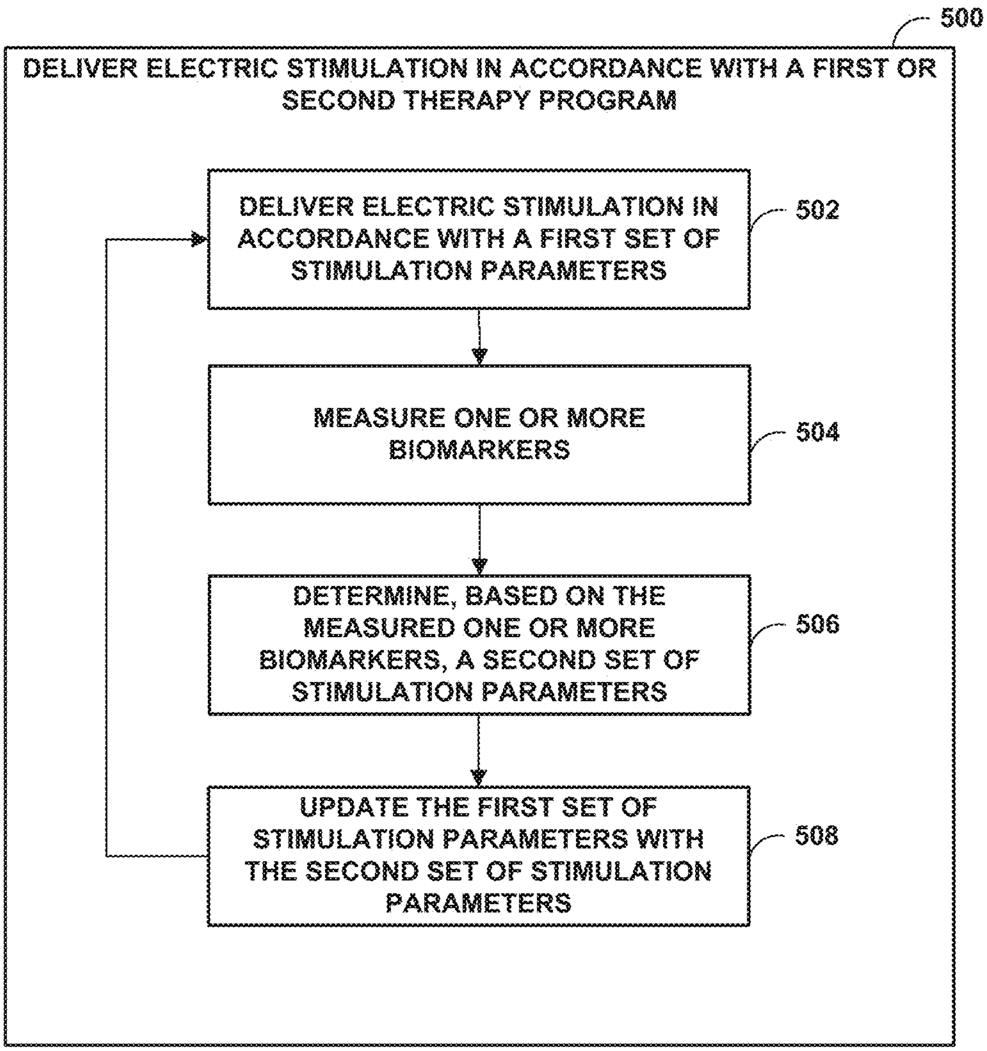
FIG. 5 is a flow diagram illustrating an example method of controlling electric stimulation, in accordance with one or more techniques of this disclosure.

FIG. 5 is a flow diagram illustrating an example method 500 of controlling electric stimulation, in accordance with one or more techniques of this disclosure. Although FIG. 5 is discussed using IMD 200A and/or IMD 200B of FIGS. 2A and 2B and external programmer 300 of FIG. 3, it is to be understood that the methods discussed herein may include and/or utilize other systems and methods in other examples. In some examples, the method 500 may be performed on its own or in conjunction with the method 400 described above. For example, method steps (402) and/or (408) may comprise the method 500.

IMD 200A may deliver electric stimulation to a patient in accordance with a first set of stimulation parameters (502). For example, the first set of stimulation parameters may include one or more programmable stimulation parameter settings defining the electrical stimulation therapy to be delivered by the IMD 200A to the patient, e.g., stimulation parameter settings 242, according to a therapy program. In some examples, stimulation parameter settings 242 may include the first set of stimulation parameters in addition to other stimulation parameters, e.g., stimulation parameters defining other therapy programs. In some examples, the first set of stimulation parameters may include an amplitude, a frequency, a pulse width, and a cycling of the electric stimulation.

IMD 200A may measure one or more biomarkers (504). In some examples, IMD 200A monitor one or more biomarkers while electric stimulation is being delivered in accordance with the first set of stimulation parameters. In other examples, IMD 200A measure one or more biomarkers after electric stimulation was delivered in accordance with the first set of stimulation parameters, e.g., the one or more biomarkers may have a delayed response and/or a long-lasting response or response according to a durable effect. For example, processing circuitry 210A may control stimulation circuitry 202 to deliver stimulation energy via electrodes 232A, 232B with the first set of stimulation parameters specified by one or more stimulation parameter settings 242 stored on storage device 212A and defined by the therapy program. Sensors 222 and/or an external device such as a patient-input device may sense and/or measure a response, e.g. biomarker data, to the delivered electric stimulation. Processing circuitry 210A may then receive the biomarker data from sensors 222 and/or other device, e.g., via telemetry circuitry 208, store biomarker data, e.g., biomarker data 254, in storage device 212A, and process the biomarker data.

In some examples, the biomarker may be at least one of a direct measure of patient symptoms, patient input, an accelerometer and/or accelerometer data, a pressure sensor and/or pressure data, a physiological signal, a cardiac signal, a heart rate, a heart rate variability, a signal and/or information related to a circadian rhythm, a blood flow, a respiratory signal, a body temperature, one or more LFPs, one or more ECAPs, a network excitability, a galvanic skin response, or any suitable biomarker for determining the efficacy of the first therapy program. For example, the biomarker may be a pain response, a pain score, an area of pain, an amount of paresthesia, an area of paresthesia, a signal and/or information relating to voiding and/or a voiding rate (e.g., voids per day), and the like. In some examples, the biomarker may be a patient posture and/or patient behavior data such as patient position, patient movement, patient movement history over a predetermined amount of time, a history of patent-selected stimulation parameters over a predetermined amount of time, and the like.

IMD 200A may determine, based on the one or more measured biomarkers, a second set of stimulation parameters (508). For example, IMD 200A may determine that the therapy program may be adjusted, as opposed to determining to deliver a different therapy program. In one example, IMD 200A may determine to increase or decrease at least one of the amplitude, pulse width, frequency, or a cycling of the electric stimulation based on a single biomarker, e.g., an ECAP and/or ECAP signal. In other examples, IMD 200A may determine to increase or decrease at least one of the amplitude, pulse width, frequency, or a cycling of the electric stimulation based on a plurality of biomarkers measured at a particular time or over a period of time.

IMD 200A may update the first set of stimulation parameters with the second set of stimulation parameters (508). For example, IMD 200A may update the therapy program to include the second set of stimulation parameters in place of the first set of stimulation parameters. IMD 200A may update and/or change stimulation parameter settings 242 to include the second set of stimulation parameters in place of the first set of stimulation parameters.

FIGS. 6-10 are a series of plots 600-1000, respectively, illustrating examples of changing from a first amount of electric stimulation that may be delivered in accordance with a first therapy program to a second amount of electric stimulation that may be delivered in accordance with a second therapy program, in accordance with one or more techniques of this disclosure. The series of plots illustrate examples of changing an amount of electric stimulation doses via changing stimulation cycle frequency, stimulation cycle duty cycle, both stimulation cycle frequency and duty cycle, and continuous and/or gradual electric stimulation change and/or transition between a first amount and a second amount.

In the examples shown in each of FIGS. 6-10, each of doses D1-D8 (and D9 in FIG. 9) are substantially similar, e.g., each having a substantially similar electrode combination, amplitude, pulse frequency and pulse width. In some examples, each of doses D1-D9 may be different from each other, e.g., having different electrode combinations, amplitudes, pulse frequencies and pulse widths, or some may be substantially the same and some may be different. Although first cycling C1 and second cycling C2 each have four doses in FIGS. 6-9, it is to be understood that first cycling C1 and second cycling C2 may include any number of doses.

Figure 6:
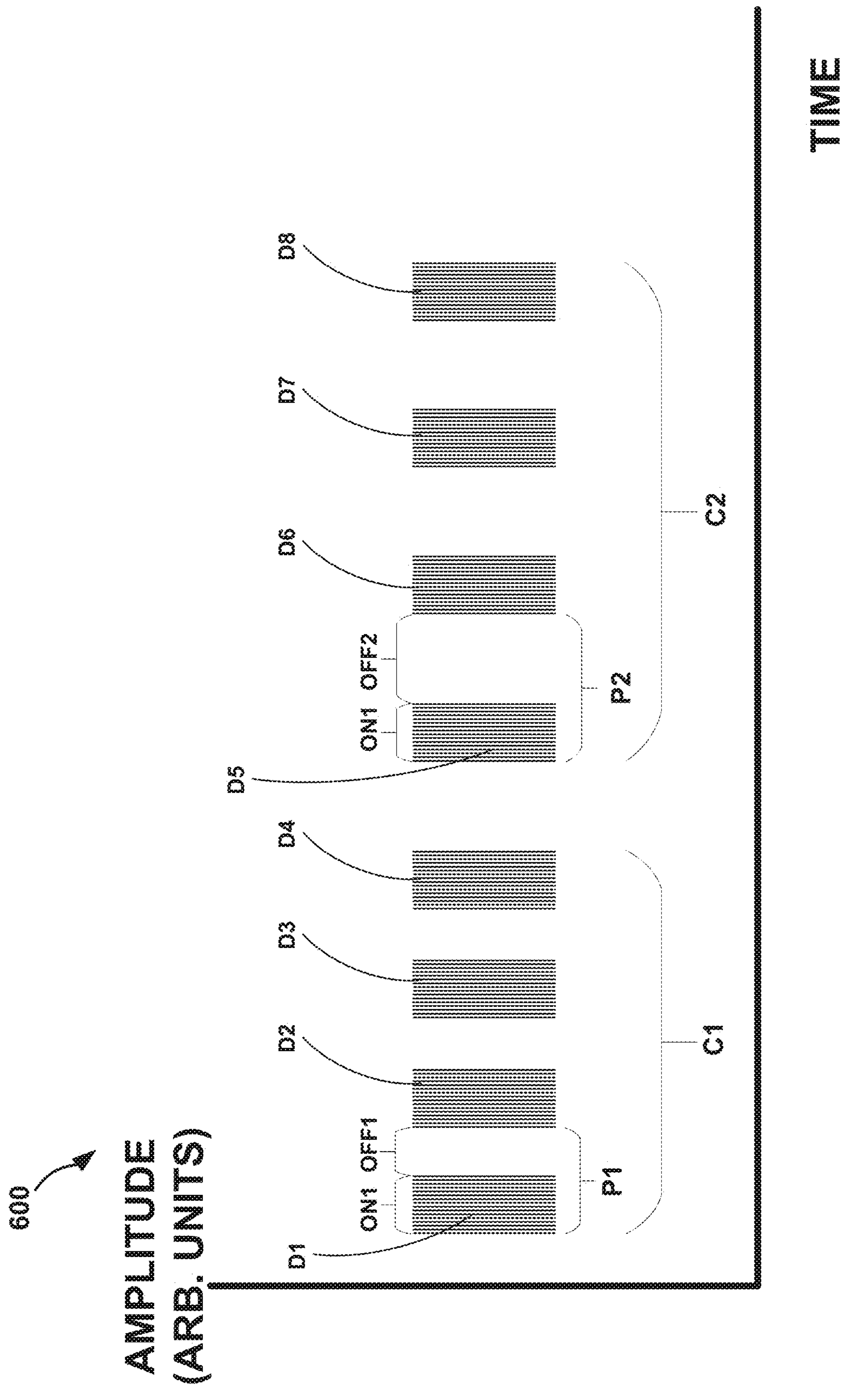
FIG. 6 is a plot of an example of changing from a first amount of electric stimulation to a second amount of electric stimulation, in accordance with one or more techniques of this disclosure.

FIG. 6 is a plot 600 of an example of changing from a first amount of electric stimulation to a second amount of electric stimulation, in accordance with one or more techniques of this disclosure. Plot 600 illustrates changing electric stimulation doses via increasing the off-time between doses, resulting in reducing the frequency of the cycling as well. In the example shown, first cycling C1 includes substantially similar doses D1-D4 each having an on-time ON1 and an off-time OFF1. The frequency of first cycling C1 is the reciprocal of the cycle period P1 (e.g., 1/P1), and the duty cycle is the ratio ON1/OFF1. Second cycling C2 includes substantially similar doses D5-D8 each having an on-time ON1 and an off-time OFF2. The frequency of second cycling C2 is the reciprocal of the cycle period P2 (e.g., 1/P2), and the duty cycle is the ratio ON1/OFF2. In the example shown, the electric stimulation is titrated down via increasing the off-time, e.g., OFF2 is greater than OFF1. As a result, an IMD delivering electric stimulation doses according to cycling C2 consumes less power than delivering electric stimulation doses according to cycling C1, and the amount of on-time over a period of time is reduced, e.g., the amount of on-time for second cycling C2 is less than for first cycling C1 over a period of time, and the cycling frequency of second cycling C2 is less than first cycling C1. Additionally, the duty cycle of the second cycling is reduced by virtue of the increase in off-time, e.g., OFF2>OFF1.

Figure 7:
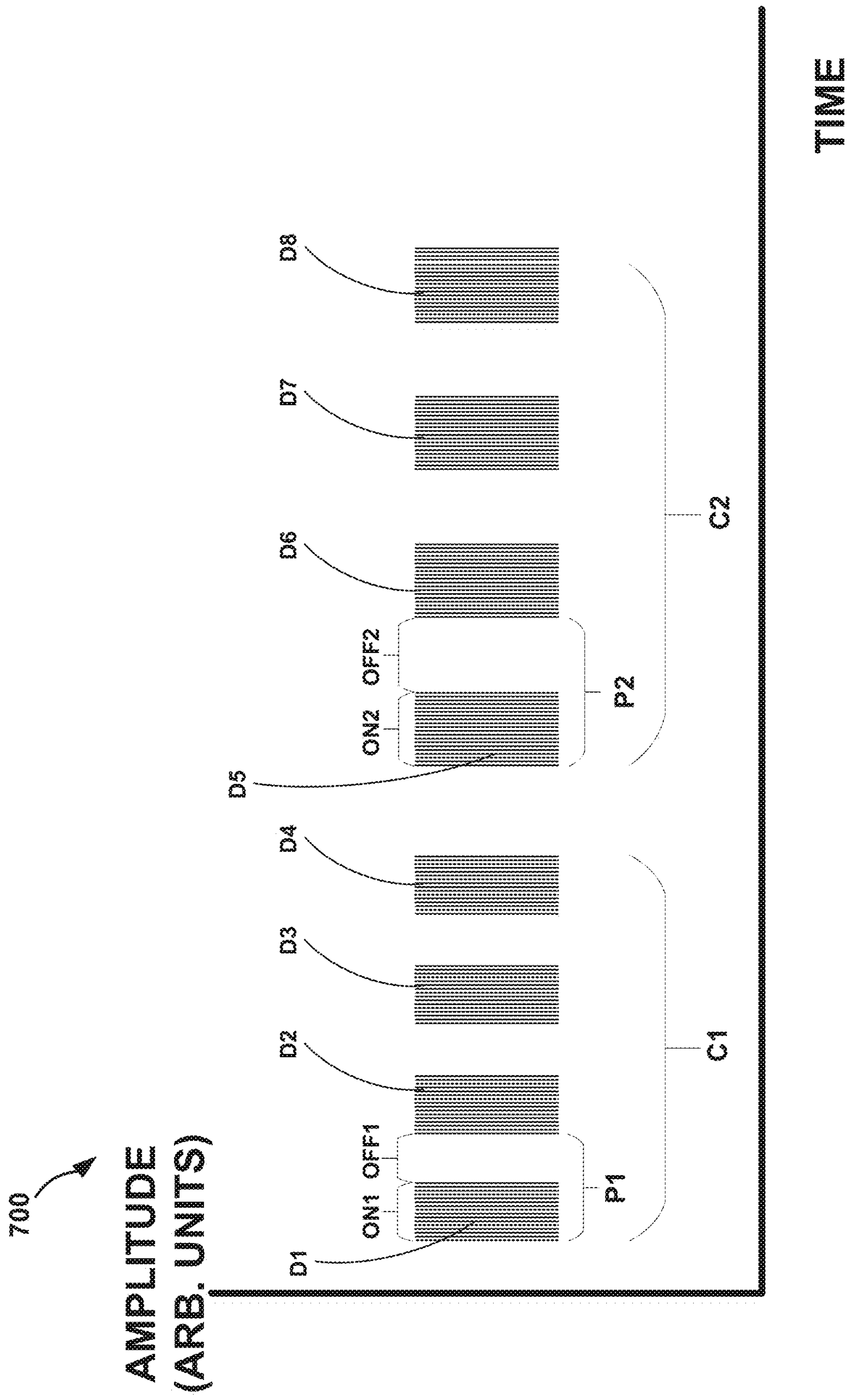
FIG. 7 is a plot of another example of changing from a first amount of electric stimulation to a second amount of electric stimulation, in accordance with one or more techniques of this disclosure.

FIG. 7 is a plot 700 of changing from a first amount of electric stimulation to a second amount of electric stimulation, in accordance with one or more techniques of this disclosure. Plot 700 illustrates changing electric stimulation doses via reducing the dosing frequency, however, the on-time of doses D5-D8 are increased to keep the duty cycle of second cycling C2 the same as C1. For example, the ratio of ON1/OFF1 may be substantially the same as ON2/OFF2 in the example of FIG. 7. Although changing electric stimulation according to the example of FIG. 7 may not necessarily reduce the stimulation and/or power consumed by an IMD delivering the stimulation over time, reducing the frequency of the stimulation may be a useful intermediate step that may allow a patient to acclimate to a reduction in the amount of stimulation therapy via further stimulation change in the future and/or to reduce the likelihood of developing a tolerance to the therapy by reducing its frequency but not the time-average of dosing received by the patient.

Figure 8:
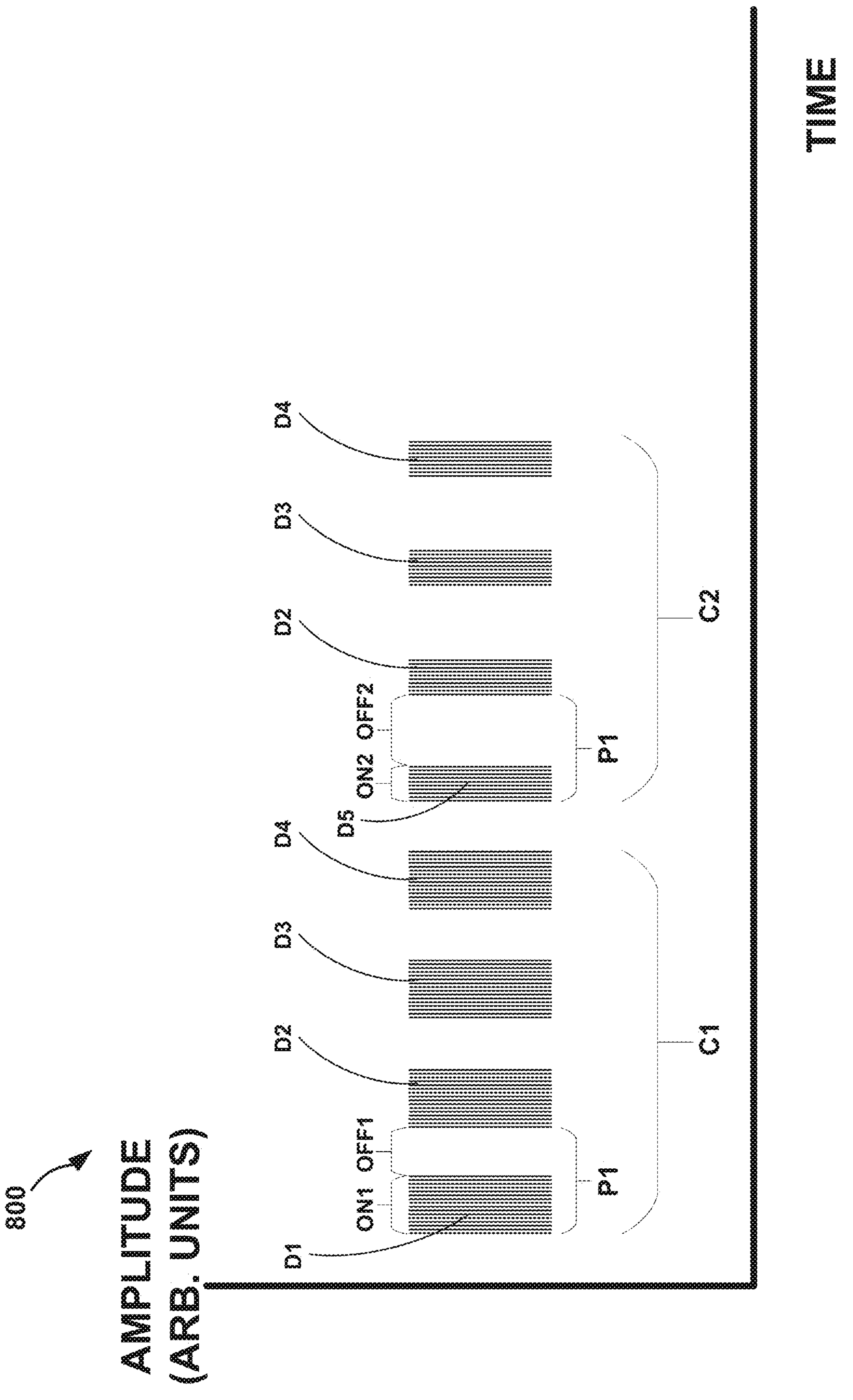
FIG. 8 is a plot of another example of changing from a first amount of electric stimulation to a second amount of electric stimulation, in accordance with one or more techniques of this disclosure.

FIG. 8 is a plot 800 of an example of changing from a first amount of electric stimulation to a second amount of electric stimulation, in accordance with one or more techniques of this disclosure. Plot 800 illustrates changing electric stimulation doses via reducing the on-time of the doses. In the example shown, the frequency of each of first cycling C1 and second cycling C2 are kept the same by virtue of increasing the off-time by the same amount as the decrease in on-time, e.g., P1=P2, however the on-time of second cycling C2 is reduced relative to first cycling C1, e.g., ON2<ON1. Consequently, the duty cycle of the second cycling is also reduced, and an IMD delivering electric stimulation doses according to cycling C2 consumes less power than delivering electric stimulation doses according to cycling C1. Additionally, the amount of on-time, for each cycle as well as over a period of time, is reduced, e.g., the amount of on-time for second cycling C2 is less than for first cycling C1.

Figure 9:
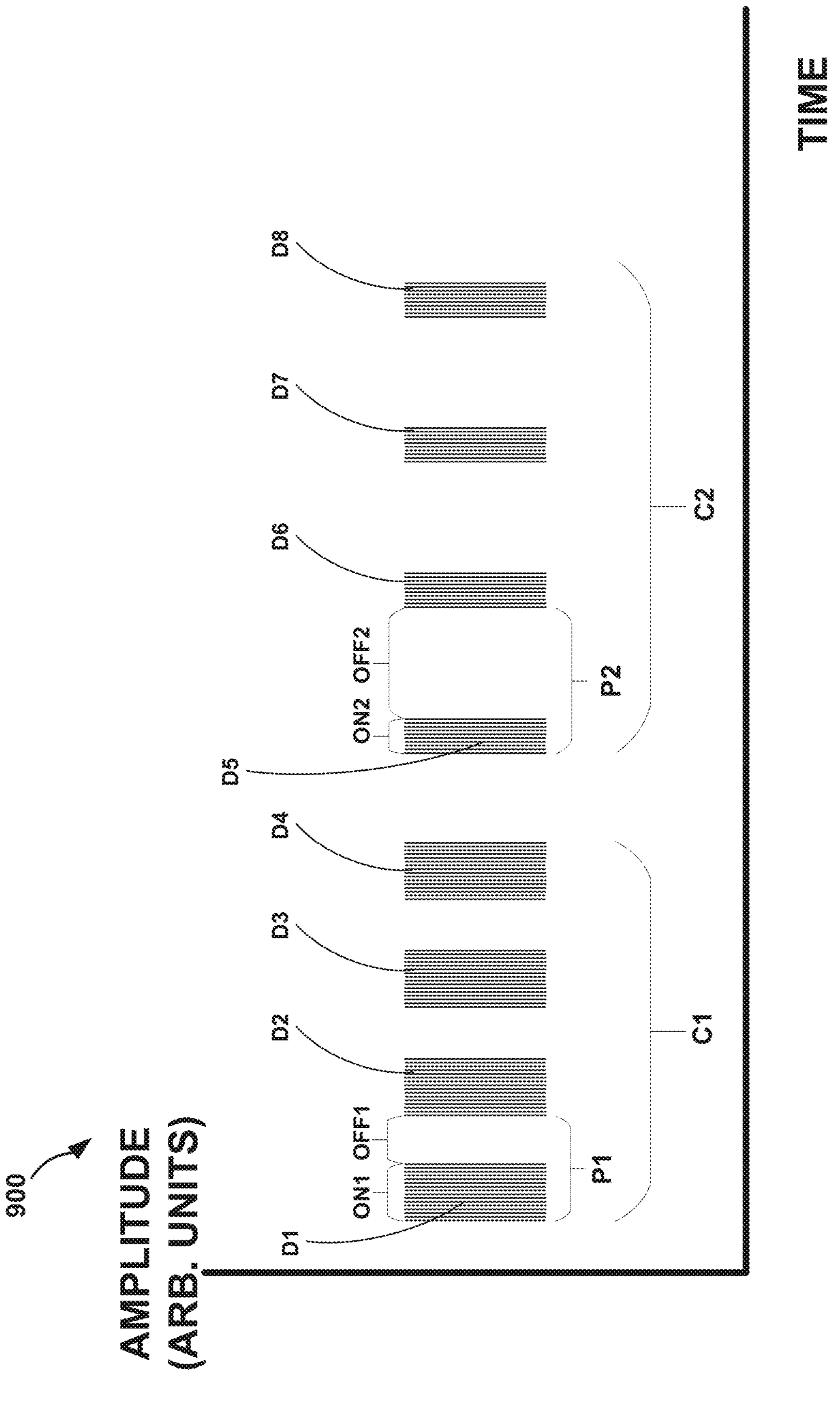
FIG. 9 is a plot of another example of changing from a first amount of electric stimulation to a second amount of electric stimulation, in accordance with one or more techniques of this disclosure.

FIG. 9 is a plot 900 of an example of changing from a first amount of electric stimulation to a second amount of electric stimulation, in accordance with one or more techniques of this disclosure. Plot 900 illustrates changing electric stimulation doses via both increasing the off-time and reducing the on-time of the doses. Namely, ON2<ON1, OFF2>OFF1, and P2>P1 (e.g., the frequency of the second cycling is reduced relative to the first cycling via an increase in the cycling period). As such, the duty cycle of the second cycling is reduced relative to the first cycling, and an IMD delivering electric stimulation doses according to cycling C2 consumes less power than delivering electric stimulation doses according to cycling C1.

Figure 10:
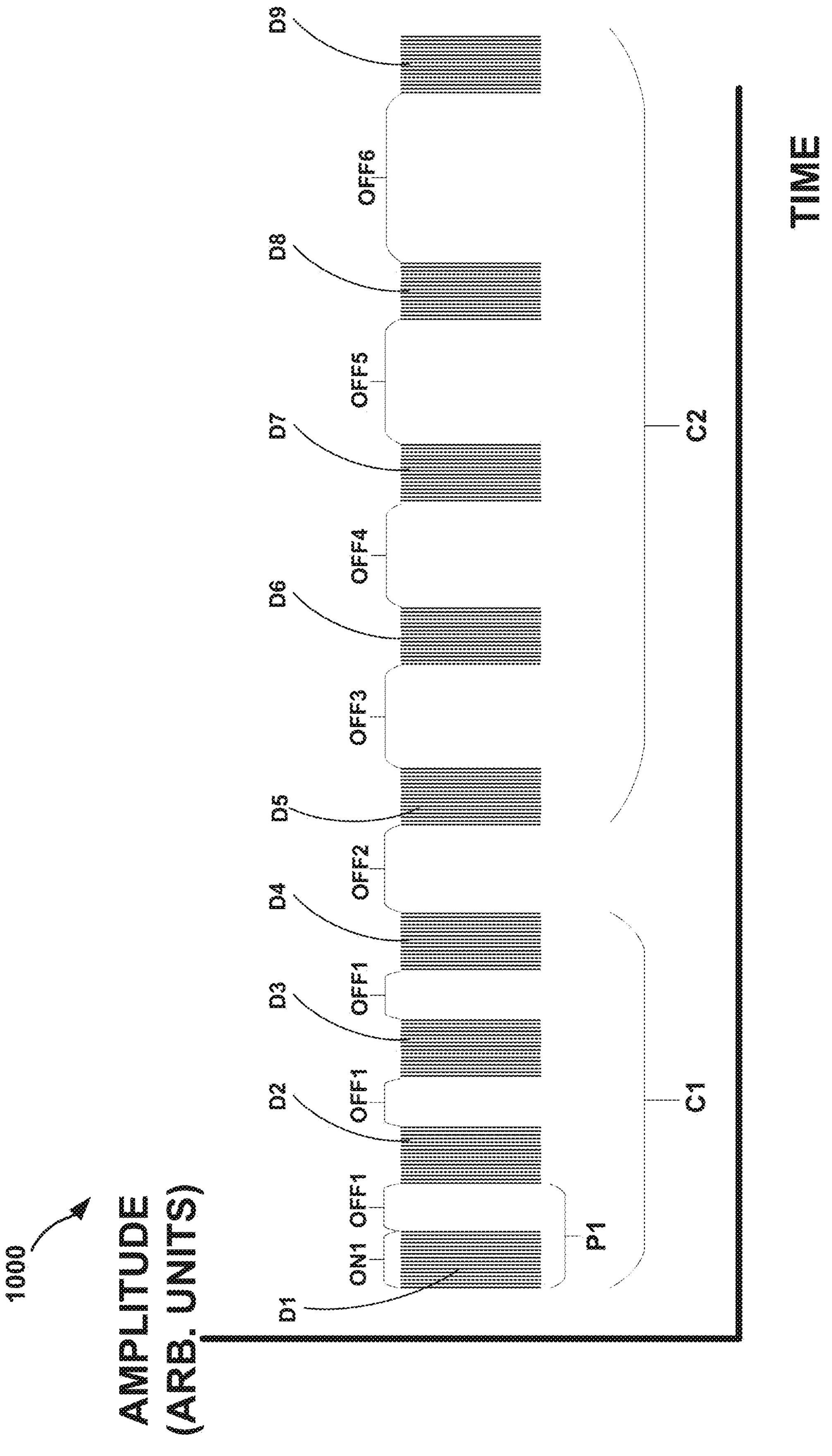
FIG. 10 is a plot of another example of changing from a first amount of electric stimulation to a second amount of electric stimulation, in accordance with one or more techniques of this disclosure.

FIG. 10 is a plot 1000 of an example of changing from a first amount of electric stimulation to a second amount of electric stimulation, in accordance with one or more techniques of this disclosure. Plot 1000 illustrates changing electric stimulation doses via a continuous taper of the electric stimulation doses by continuously increasing the off-time between the doses, e.g., OFF1<OFF2<OFF3<OFF4<OFF5<OFF6. For example, IMD 200A may transition from the first therapy program to the second therapy program in response to the biomarker satisfying the threshold (e.g., as at (408) above) gradually over a period of time rather than immediately or within a short period of time. In the example shown, the first four does D1-D4 are delivered according to first cycling C1 with an on-time ON1, an off-time OFF1, a cycling frequency 1/P1, and a cycling duty cycle ON1/OFF1. In the example shown, the second cycling C2 does not have a constant period or off-time, but rather both increase between each of doses D5-D9. In the example shown, the on-times ON1 of all doses D1-D9 are substantially the same, however, it need not be so, and in some examples the on-time of any of doses D5-D9 may be increased and or decreased relative to ON1. In the example shown, the amount of electric stimulation delivered over the time period of second cycling C2 continuously decreases via the continuous increase in off-time and a continuous decrease in cycling frequency. In some examples, second cycling C2 may continuously decrease the on-time. In the example shown, an IMD delivering electric stimulation doses according to cycling C2 consumes less power than delivering electric stimulation doses according to cycling C1.

Figure 11:
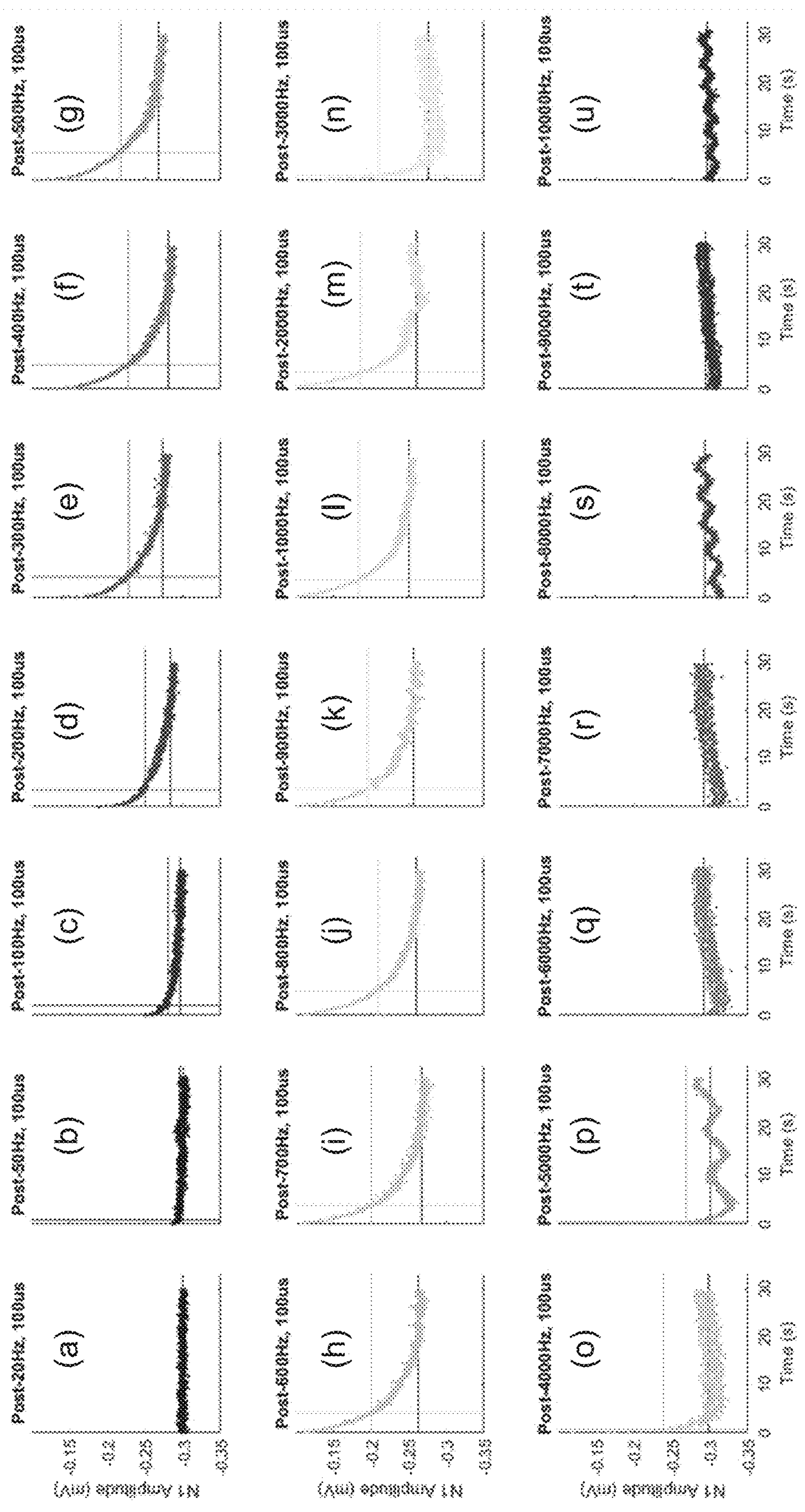
FIG. 11 is a series of plots illustrating one or more example features of an ECAP biomarker, in accordance with one or more techniques of this disclosure.

FIG. 11 is a series of plots (a)-(u) illustrating one or more example features of an ECAP biomarker, in accordance with one or more techniques of this disclosure. Each of plots (a)-(u) are a plot of the amplitude of the N1 ECAP in millivolts (mV) for 100 microseconds following 30 seconds of electric stimulation at the frequency denoted on each plot (a)-(u). In other words, the series of plots illustrate the response of the N1 ECAP signal following stimulation as a function of frequency of the electric stimulation, with the stimulation frequency increasing from plot (a) at 20 Hz to plot (u) at 10 kHz. In the example shown, the N1 ECAP amplitude decreases significantly following stimulation at certain frequencies then settles to a constant value following an amount of time that depends on the stimulation frequency. In some examples, the amount of time to return to baseline may be a biomarker that may be monitored, e.g., such as at (404) and (408) of method 400. In some examples, electric stimulation may be delivered at a lower power to monitor ECAP data such as the N1 amplitude.

Figure 12A:
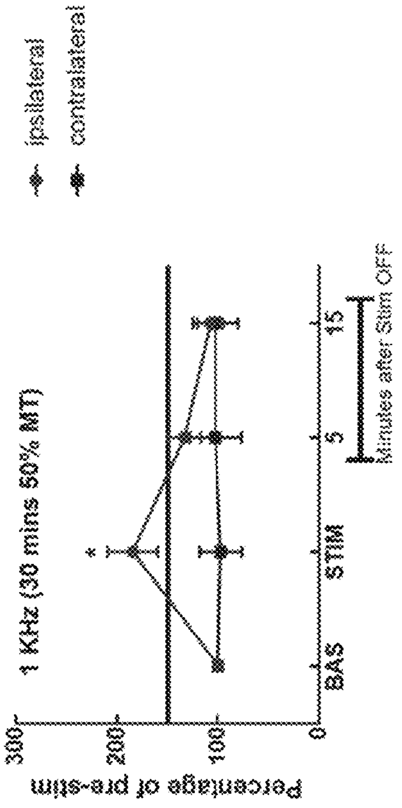
FIG. 12A is a plot of an example feature of a biomarker after electric stimulation comprising a 1 kHz frequency, in accordance with one or more techniques of this disclosure.
Figure 12B:
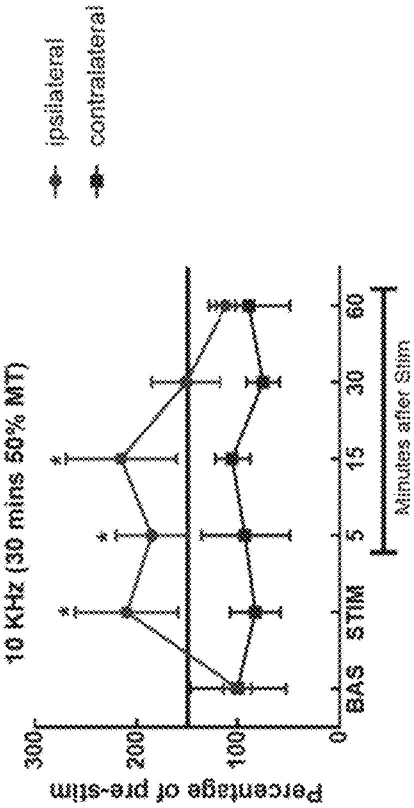
FIG. 12B is a plot of another example feature of the biomarker of FIG. 12A after electric stimulation comprising a 10 kHz frequency, in accordance with one or more techniques of this disclosure.

FIG. 12A is a plot of an example feature of a biomarker after electric stimulation comprising a 1 kHz frequency, in accordance with one or more techniques of this disclosure. FIG. 12B is a plot of another example feature of the biomarker of FIG. 12A after electric stimulation comprising a 10 kHz frequency, in accordance with one or more techniques of this disclosure. In the examples of both FIGS. 11A and 11B, a reflex marker as a measure of pain is shown as a function of time after electric stimulation has ended, the time at which the stimulation ended being denoted as STIM on the x-axis of both plots. In some examples, a carry-over effect, e.g., therapy efficacy that continues after stimulation has been turned off or put into a low or lower power delivery program. In the examples shown, the carry-over effect after 30 minutes of electric stimulation at 1 kHz (FIG. 11A) is minimal while the carry-over effect after 30 minutes of stimulation at 10 kHz (FIG. 11B) lasts for at least 15 minutes. In some examples, carry-over effect may be a biomarker that may be monitored, e.g., such as at (404) and (408) of method 400.

The following numbered examples may illustrate one or more aspects of this disclosure:

Example 1: A method of cycling electric stimulation includes delivering, via an implantable device, electric stimulation to a patient in accordance with a first therapy program; monitoring, via the implantable device and while the electric stimulation is being delivered in accordance with the first therapy program, a biomarker; and responsive to determining the biomarker satisfies a threshold, delivering, via the implantable device, electric stimulation to the patient in accordance with a second therapy program that is different than the first therapy program.

Example 2: The method of example 1, wherein the biomarker comprises a first biomarker, the method further includes monitoring, via the implantable device and while the electric stimulation is being delivered in accordance with the second therapy program, a second biomarker.

Example 3: The method of example 2, wherein the first biomarker and the second biomarker are different biomarkers.

Example 4: The method of any of examples 2 and 3, wherein the first biomarker and the second biomarker are the same biomarker.

Example 5: The method of example 4, further includes responsive to determining the second biomarker satisfies the threshold, delivering, via the implantable device, electric stimulation to the patient in accordance with a first therapy program.

Example 6: The method of any of examples 4 and 5, wherein the threshold comprises a first threshold, the method further includes responsive to determining the second biomarker satisfies a second threshold, delivering, via the implantable device, electric stimulation to the patient in accordance with a first therapy program.

Example 7: The method of any one of examples 1-6, wherein delivering electric stimulation via the second therapy program comprises not delivering electric stimulation to the patient.

Example 8: The method of any one of examples 1-7, wherein the first therapy program comprises electric stimulation comprising at least one frequency of at least 10 kHz.

Example 9: The method of any one of examples 1-8, wherein the biomarker comprises at least one of a direct measure of symptoms, an accelerometer, a pressure sensor, a physiological signal, a cardiac signal, a respiratory signal, a body temperature, a patient posture, or an evoked compound action potential (ECAP).

Example 10: The method of any one of examples 1-9, wherein the first therapy program comprises a first amount of electric stimulation, wherein the second therapy program comprises a second amount of electric stimulation, wherein the second amount of electric stimulation is less than the first amount of electric stimulation.

Example 11: The method of example 10, wherein the second amount of electric stimulation is sufficient for capturing an evoked compound action potential (ECAP).

Example 12: A system includes cause the implantable device to deliver electric stimulation to a patient in accordance with a first therapy program; monitor, via the implantable device and while the electric stimulation is being delivered in accordance with the first therapy program, a biomarker; and responsive to determining the biomarker satisfies a threshold, cause the implantable device to deliver electric stimulation to the patient in accordance with a second therapy program.

Example 13: The system of example 12, wherein the biomarker comprises a first biomarker, the processing circuitry further configured to: monitor, via the implantable device and while the electric stimulation is being delivered in accordance with the second therapy program, a second biomarker.

Example 14: The system of example 13, wherein the first biomarker and the second biomarker are the same biomarker.

Example 15: The system of example 14, the processing circuitry further configured to: responsive to determining the second biomarker satisfies the threshold, cause the implantable device to deliver electric stimulation to the patient in accordance with the first therapy program.

Example 16: The system of any one of examples 12-15, wherein the second therapy program comprises not delivering electric stimulation to the patient.

Example 17: The system of any one of examples 12-16, wherein the biomarker comprises at least one of a direct measure of symptoms, an accelerometer, a pressure sensor, a physiological signal, a cardiac signal, a respiratory signal, a body temperature, a patient posture, or an evoked compound action potential (ECAP).

Example 18: The system of any one of examples 12-17, wherein the first therapy program comprises a first amount of electric stimulation, wherein the second therapy program comprises a second amount of electric stimulation, where the second amount of electric stimulation is less than the first amount of electric stimulation.

Example 19: The system of example 18, wherein the second amount of electric stimulation is sufficient for capturing an evoked compound action potential (ECAP).

Example 20: A computer readable medium includes cause an implantable device to deliver electric stimulation to a patient in accordance with a first therapy program; monitoring, via the implantable device and while the electric stimulation is being delivered in accordance with the first therapy program, a biomarker; and responsive to determining the biomarker satisfies a threshold, cause the implantable device to deliver electric stimulation to the patient in accordance with a second therapy program.

The techniques described in this disclosure may be implemented, at least in part, in hardware, software, firmware or any combination thereof. For example, various aspects of the described techniques may be implemented within processing circuitry, which may include one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term “processor” or “processing circuitry” may generally refer to any of the foregoing logic circuitry, alone or in combination with other logic circuitry, or any other equivalent circuitry. A control unit including hardware may also form one or more processors or processing circuitry configured to perform one or more of the techniques of this disclosure.

Such hardware, software, and firmware may be implemented, and various operation may be performed within same device, within separate devices, and/or on a coordinated basis within, among or across several devices, to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components. Processing circuitry described in this disclosure, including a processor or multiple processors, may be implemented, in various examples, as fixed-function circuits, programmable circuits, or a combination thereof. Fixed-function circuits refer to circuits that provide particular functionality with preset operations. Programmable circuits refer to circuits that can be programmed to perform various tasks and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive stimulation parameters or output stimulation parameters), but the types of operations that the fixed-function circuits perform are generally immutable. In some examples, one or more of the units may be distinct circuit blocks (fixed-function or programmable), and in some examples, one or more of the units may be integrated circuits.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

What is claimed is:

1. A method of cycling electric stimulation, the method comprising:

delivering, via an implantable device, electric stimulation to a patient in accordance with a first therapy program;

monitoring, via the implantable device and while the electric stimulation is being delivered in accordance with the first therapy program, a biomarker;

responsive to determining the biomarker satisfies a threshold, delivering, via the implantable device, electric stimulation to the patient in accordance with a second therapy program that is different than the first therapy program; and responsive to determining the biomarker does not satisfy the threshold after delivering the electrical stimulation in accordance with the second therapy program, delivering, via the implantable device, electric stimulation to the patient in accordance with the first therapy program.

2. The method of claim 1, wherein the biomarker comprises a first biomarker, the method further comprising:

monitoring, via the implantable device and while the electric stimulation is being delivered in accordance with the second therapy program, a second biomarker.

3. The method of claim 2, wherein the first biomarker and the second biomarker are different biomarkers.

4. The method of claim 2, wherein the first biomarker and the second biomarker are the same biomarker.

5. The method of claim 4, wherein the threshold comprises a first threshold, the method further comprising:

responsive to determining the second biomarker satisfies a second threshold, delivering, via the implantable device, electric stimulation to the patient in accordance with the first therapy program.

6. The method of claim 1, wherein delivering electric stimulation via the second therapy program comprises not delivering electric stimulation to the patient.

7. The method of claim 1, wherein the first therapy program comprises electric stimulation comprising at least one frequency of at least 10 kHz.

8. The method of claim 1, wherein the biomarker comprises at least one of a direct measure of symptoms, an accelerometer, a pressure sensor, a physiological signal, a cardiac signal, a respiratory signal, a body temperature, a patient posture, or an evoked compound action potential (ECAP).

9. The method of claim 1, wherein the first therapy program comprises a first amount of electric stimulation, wherein the second therapy program comprises a second amount of electric stimulation, wherein the second amount of electric stimulation is less than the first amount of electric stimulation.

10. The method of claim 9, wherein the second amount of electric stimulation is sufficient for capturing an evoked compound action potential (ECAP).

11. The method of claim 9, wherein the first amount of electric stimulation comprises a first plurality of stimulation doses having a first on-time and a first off-time, wherein the second amount of electric stimulation comprises a second plurality of stimulation doses having a second on-time less than the first on-time and a second off-time greater than the first off-time.

12. The method of claim 9, wherein the first amount of electric stimulation comprises a first plurality of stimulation doses having a first on-time and a first off-time, wherein the second amount of electric stimulation comprises a second plurality of stimulation doses having the first on-time and a plurality of second off-times that increase between subsequent stimulation doses of the second plurality of stimulation doses.

13. A system comprising:

an implantable device comprising electrodes configured to deliver electrical stimulation to a patient; and a device comprising processing circuitry configured to:

cause the implantable device to deliver electric stimulation to a patient in accordance with a first therapy program;

monitor, via the implantable device and while the electric stimulation is being delivered in accordance with the first therapy program, a biomarker; and responsive to determining the biomarker satisfies a threshold, cause the implantable device to deliver electric stimulation to the patient in accordance with a second therapy program; and responsive to determining the biomarker does not satisfy the threshold after delivering the electrical stimulation in accordance with the second therapy program, cause the implantable device to deliver electric stimulation to the patient in accordance with the first therapy program.

14. The system of claim 13, wherein the biomarker comprises a first biomarker, the processing circuitry further configured to:

monitor, via the implantable device and while the electric stimulation is being delivered in accordance with the second therapy program, a second biomarker.

15. The system of claim 14, wherein the first biomarker and the second biomarker are the same biomarker.

16. The system of claim 15, wherein the threshold comprises a first threshold, the processing circuitry further configured to:

responsive to determining the second biomarker satisfies a second threshold, cause the implantable device to deliver electric stimulation to the patient in accordance with the first therapy program.

17. The system of claim 13, wherein the second therapy program comprises not delivering electric stimulation to the patient.

18. The system of claim 13, wherein the biomarker comprises at least one of a direct measure of symptoms, an accelerometer, a pressure sensor, a physiological signal, a cardiac signal, a respiratory signal, a body temperature, a patient posture, or an evoked compound action potential (ECAP).

19. The system of claim 13, wherein the first therapy program comprises a first amount of electric stimulation, wherein the second therapy program comprises a second amount of electric stimulation, where the second amount of electric stimulation is less than the first amount of electric stimulation.

20. The system of claim 19, wherein the second amount of electric stimulation is sufficient for capturing an evoked compound action potential (ECAP).

21. A computer readable medium comprising instructions that when executed cause one or more processors to:

cause an implantable device to deliver electric stimulation to a patient in accordance with a first therapy program;

monitoring, via the implantable device and while the electric stimulation is being delivered in accordance with the first therapy program, a biomarker; and responsive to determining the biomarker satisfies a threshold, cause the implantable device to deliver electric stimulation to the patient in accordance with a second therapy program; and responsive to determining the biomarker does not satisfy the threshold after delivering the electrical stimulation in accordance with the second therapy program, cause the implantable device to deliver electric stimulation to the patient in accordance with the first therapy program.

* * * * *